(12) United States Patent
Shi et al.

(10) Patent No.: US 7,425,442 B2
(45) Date of Patent: Sep. 16, 2008

(54) PHYTATE POLYNUCLEOTIDES AND METHODS OF USE

(75) Inventors: Jinrui Shi, Johnston, IA (US); Hongyu Wang, Urbandale, IA (US); Yunsheng Wu, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 379 days.

(21) Appl. No.: 11/069,623

(22) Filed: Mar. 1, 2005

(65) Prior Publication Data

US 2005/0202486 A1  Sep. 15, 2005

Related U.S. Application Data

(62) Division of application No. 10/255,817, filed on Sep. 26, 2002, now abandoned.

(60) Provisional application No. 60/325,308, filed on Sep. 27, 2001.

(51) Int. Cl.
*C12N 15/82* (2006.01)
*C12N 15/52* (2006.01)
*C12N 15/12* (2006.01)

(52) U.S. Cl. .................. 435/320.1; 536/23.2; 536/23.6

(58) Field of Classification Search .................. None
See application file for complete search history.

(56) References Cited

U.S. PATENT DOCUMENTS 6,197,561 B1  3/2001  Martino-Catt et al.
2003/0009011 A1  1/2003  Shi et al.

FOREIGN PATENT DOCUMENTS

WO  WO 99/05298 A1  2/1999
WO  WO9955879  *  4/1999
WO  WO 99/55879  11/1999

OTHER PUBLICATIONS

Guo et al. 2004, Proc. Natl. Acad. Sci. USA 101:9205-9210.*
Lazar et al. 1988, Mol. Cell. Biol. 8:1247-1252.*
Falcon-Perez JM et al. 1999, J Biol Chem. 274:23584-90.*
Hill et al 1998, Biochem. Biophys. Res. Comm. 244:573-577.*
Brearley, Charles A. et al., Metabolic Relations of Inositol 3,4,5,6-Tetrakisphosphate Revealed by Cell Permeabilization. Identification of Inositol 3,4,5,6-Tetrakisphosphate 1-Kinase and Inositol 3,4,5,6-Tetrakisphosphate Phosphate Activities in Mesophyll Cells, Plant Physiol. 122:1209-1216, Apr. 2000.
Field, Jessica et al., An Entamoeba histolytica inositol 1,3,4-trisphosphate 5/6-kinase has a novel 3-kinase activity, Mol. Biochem. Parasitol. 108: 119-123, 2000.
Larson, Steve R. et al., Isolation and Genetic Mapping of a Non-Lethal Rice (Orzyza sativa L.), Crop. Sci. 401:1397-1405, 2000.
Phillippy, Brian Q., Identification of Inositol 1,3,4-Trisphosphate 5-Kinase and Inositol 1,3,4,5- Tetrakisphosphate 6-Kinase in Immature Soybean Seeds, Plant Physiol. 116:291-297, 1998.
Raboy, Victor et al., Origin and Seed Phenotype of Maize low phytic acid 1-1 and low phytic acid 2-1, Plant Physiol. 124:355-368, Sep. 2000.
Rasmussen, S.K. et al., Identificationof two-phytate barley (Hordeum vulgare L.) grain mutants by TLC and genetic analysis, Hereditas 129:107-112, 1998.
Wilcox, James R., et al., Isolation of High Seed Inorganic P, Low-Phytate Soybean Mutants, Crop Sci. 40:1601-1605, 2000.
Wilson, Monita P. et al., Isolation of Inositol 1,3,4-Trisphosphate 5/6-Kinase, cDNA Cloning, and Expression of the Recombinant Enzyme, J. Biol. Chem. 271(20):11904-11910, 1996.
Wilson, Monita P. et al., Characterization of cDNA Encoding Arabidopsis thaliana Inositol 1,3,4-trisphosphate 5/6-kinase, Biochem. Biophys. Res. Commun. 232:678-681, 1997.
Yang, Xiaonian et al., Multitasking in signal transduction by a promiscuous human Ins (3,4,5,6)P 1-kinase/Ins (1,3,4)P 5/6-kinase, Biochem. J. 351:551-555, 2000.
NCBI Database Accession No. AC004005.
NCBI Database Accession No. 8G49605.
NCBI Database Accession No. AL031394.
NCBI Database Accession No. AF080173.
NCBI Database Accession No. AF079853.
NCBI Database Accession No. AI586617.
NCBI Database Accession No. BG158108.
NCBI Database Accession No. AI603721.
NCBI Database Accession No. AF188610.
NCBI Database Accession No. C72860.
NCBI Database Accession No. BE361672.
NCBI Database Accession No. AC069324.
NCBI Database Accession No. BG604271.
NCBI Database Accession No. BE517259.
NCBI Database Accession No. AW324653.
NCBI Database Accession No. BE345000.

* cited by examiner

*Primary Examiner*—Stuart F. Baum
*Assistant Examiner*—Li Zheng
(74) *Attorney, Agent, or Firm*—Pioneer Hi-Bred International, Inc.; Kathryn K. Lappegard

(57) ABSTRACT

This invention relates to newly identified polynucleotides and polypeptides in the phytic acid biosynthetic pathway, fragments, variants and derivatives of same; methods for making the polynucleotides, polypeptides, fragments, variants, derivatives and antagonists. In particular the invention relates to polynucleotides and polypeptides of the inositol 1,3,4-trisphosphate 5/6-kinase gene family. In particular this invention relates to using the newly identified polynucleotides and polypeptides to modulate the phytic acid biosynthesis in such a way as to decrease phytate and/or increase non-phytate phosphorous, especially in corn or soy animal feedstuffs.

5 Claims, No Drawings

SEQUENCE LISTING

```
<160> NUMBER OF SEQ ID NOS: 29

<210> SEQ ID NO 1
<211> LENGTH: 1458
<212> TYPE: DNA
<213> ORGANISM: Zea mays
<220> FEATURE:
<221> NAME/KEY: CDS
<222> LOCATION: (224)...(1270)

<400> SEQUENCE: 1
gcacgagcct tgccctgccc gcacacacca cctgtccccg cacggccgca ccgctccgct      60
cccgaggctt agggctccgg ccgcgctccc ttccctccc ggcattcccg atctctcgcc     120
gccgcccgcc tggccttgat ctcgatcgcc ctccctctc cgctctcgct ccggcaggcc     180
ggcccgggtt tgtctcgccg ctattgggcc tcggcacgct gcg atg gtg tcg ggc      235
```

|  |  |
|---|---|
|                                                    Met Val Ser Gly<br>                                                     1 |  |
| gtg tgc gtg ggg acg gag ggg cag gtg gac cct gag gcg gtg gcg ccg<br>Val Cys Val Gly Thr Glu Gly Gln Val Asp Pro Glu Ala Val Ala Pro<br> 5                         10                     15                    20 | 283 |
| gct gtc gcg gag gag gcg gtg gtg ccg gcg ccc gcg agg gag gtc gtg<br>Ala Val Ala Glu Glu Ala Val Val Pro Ala Pro Ala Arg Glu Val Val<br>                 25                     30                     35 | 331 |
| gtg ggg tac gcg ctc acg agt aag aag gcc aag agc ttc ctc caa ccc<br>Val Gly Tyr Ala Leu Thr Ser Lys Lys Ala Lys Ser Phe Leu Gln Pro<br>                 40                     45                     50 | 379 |
| aag ctc cgg ggg ctc gcc agg aaa aag gga atc ttg ttt gtc gct att<br>Lys Leu Arg Gly Leu Ala Arg Lys Lys Gly Ile Leu Phe Val Ala Ile<br>            55                     60                     65 | 427 |
| gat cag aaa cgc cca ttg tct gat caa ggt cca ttt gac att gtt ctt<br>Asp Gln Lys Arg Pro Leu Ser Asp Gln Gly Pro Phe Asp Ile Val Leu<br> 70                         75                     80 | 475 |
| cat aag ttg act gga agg ggg tgg cag caa ttg ctg gag gaa tat agg<br>His Lys Leu Thr Gly Arg Gly Trp Gln Gln Leu Leu Glu Glu Tyr Arg<br> 85                         90                     95                  100 | 523 |
| gag gca cac cca gaa gtt act gtt ctt gat cca cct ggc gca ata gca<br>Glu Ala His Pro Glu Val Thr Val Leu Asp Pro Pro Gly Ala Ile Ala<br>                105                   110                   115 | 571 |
| aac ttg ctt gat cgc cag tct atg ctt caa gaa gta tct gaa ttg gac<br>Asn Leu Leu Asp Arg Gln Ser Met Leu Gln Glu Val Ser Glu Leu Asp<br>           120                    125                   130 | 619 |
| ctc aca gat tgt cat ggt aaa gta cgt gtg cct aag cag cta ttc gtt<br>Leu Thr Asp Cys His Gly Lys Val Arg Val Pro Lys Gln Leu Phe Val<br>           135                    140                   145 | 667 |
| aat act gat ccc tca tca ata cca gct gca gtt agg agg gca ggt ctc<br>Asn Thr Asp Pro Ser Ser Ile Pro Ala Ala Val Arg Arg Ala Gly Leu<br>          150                    155                   160 | 715 |
| tct ctc cca ttg gtg gca aaa ccc ttg gtg gcg aag tcc cat gag cta<br>Ser Leu Pro Leu Val Ala Lys Pro Leu Val Ala Lys Ser His Glu Leu<br>165                     170                    175                   180 | 763 |
| tcc ctt gct tat gat cca act tca ctg acc aaa ctt gag ccc ccc ttg<br>Ser Leu Ala Tyr Asp Pro Thr Ser Leu Thr Lys Leu Glu Pro Pro Leu<br>                185                   190                   195 | 811 |
| gtt ctt cag gaa ttt gtt aac cat ggt ggc gtc atg ttt aag gtg tac<br>Val Leu Gln Glu Phe Val Asn His Gly Gly Val Met Phe Lys Val Tyr<br>          200                    205                   210 | 859 |
| att gtt ggg gat gca ata agg gtt gta cgt cga ttt tca ctc cca aat<br>Ile Val Gly Asp Ala Ile Arg Val Val Arg Arg Phe Ser Leu Pro Asn<br>          215                    220                   225 | 907 |
| gtt gat gaa ggc gat cta tcg aac aat gct ggg gta ttt cgg ttt cca<br>Val Asp Glu Gly Asp Leu Ser Asn Asn Ala Gly Val Phe Arg Phe Pro<br>          230                    235                   240 | 955 |
| agg gtc tct tgt gct gca gcc agt gca gat gat gca gat ctt gac cct<br>Arg Val Ser Cys Ala Ala Ala Ser Ala Asp Asp Ala Asp Leu Asp Pro<br>245                     250                    255                   260 | 1003 |
| cgt gtt gct gaa ctt cct ccg aga cca ttg ctt gag atc ttg gca cga<br>Arg Val Ala Glu Leu Pro Pro Arg Pro Leu Leu Glu Ile Leu Ala Arg<br>                265                   270                   275 | 1051 |
| gag ctg cgc cga cga ctg ggt ctt aga cta ttc aac atc gat atg att<br>Glu Leu Arg Arg Arg Leu Gly Leu Arg Leu Phe Asn Ile Asp Met Ile<br>          280                    285                   290 | 1099 |
| agg gag cat ggg acg cga gat cgg ttt tat gtc ata gac atg aac tac<br>Arg Glu His Gly Thr Arg Asp Arg Phe Tyr Val Ile Asp Met Asn Tyr<br>                295                   300                   305 | 1147 |

```
ttt cct ggg tac ggc aaa atg cct gga tac gag cac gtg ttc acc gac     1195
Phe Pro Gly Tyr Gly Lys Met Pro Gly Tyr Glu His Val Phe Thr Asp
    310                 315                 320 ttc ctg ctg agc ctt gcc aag aaa gag tac aag aga cga caa agc tat     1243
Phe Leu Leu Ser Leu Ala Lys Lys Glu Tyr Lys Arg Arg Gln Ser Tyr
325                 330                 335                 340 agc tcg cta agc tca ggc gaa tgg tga taagcgagga gactactcgg           1290
Ser Ser Leu Ser Ser Gly Glu Trp  *
                345 cggggcatgt atatgtctat catccacgat gcgtgcgtac agatgtactt gtgcatgacg   1350 agagataatg ggtcgtagaa gcggagggct gttgtcaggc ataactaac tgttgcttta    1410 catgtgctaa ctgttgatgc ttcagaataa attttgtttg ggtggaaa                1458

<210> SEQ ID NO 2
<211> LENGTH: 348
<212> TYPE: PRT
<213> ORGANISM: Zea mays

<400> SEQUENCE: 2

Met Val Ser Gly Val Cys Val Gly Thr Glu Gly Gln Val Asp Pro Glu
 1               5                  10                  15

Ala Val Ala Pro Ala Val Ala Glu Glu Ala Val Pro Ala Pro Ala
             20                  25                  30

Arg Glu Val Val Val Gly Tyr Ala Leu Thr Ser Lys Lys Ala Lys Ser
         35                  40                  45

Phe Leu Gln Pro Lys Leu Arg Gly Leu Ala Arg Lys Lys Gly Ile Leu
     50                  55                  60

Phe Val Ala Ile Asp Gln Lys Arg Pro Leu Ser Asp Gln Gly Pro Phe
 65                  70                  75                  80

Asp Ile Val Leu His Lys Leu Thr Gly Arg Gly Trp Gln Gln Leu Leu
                 85                  90                  95

Glu Glu Tyr Arg Glu Ala His Pro Glu Val Thr Val Leu Asp Pro Pro
            100                 105                 110

Gly Ala Ile Ala Asn Leu Leu Asp Arg Gln Ser Met Leu Gln Glu Val
        115                 120                 125

Ser Glu Leu Asp Leu Thr Asp Cys His Gly Lys Val Arg Val Pro Lys
    130                 135                 140

Gln Leu Phe Val Asn Thr Asp Pro Ser Ser Ile Pro Ala Ala Val Arg
145                 150                 155                 160

Arg Ala Gly Leu Ser Leu Pro Leu Val Ala Lys Pro Leu Val Ala Lys
                165                 170                 175

Ser His Glu Leu Ser Leu Ala Tyr Asp Pro Thr Ser Leu Thr Lys Leu
            180                 185                 190

Glu Pro Pro Leu Val Leu Gln Glu Phe Val Asn His Gly Gly Val Met
        195                 200                 205

Phe Lys Val Tyr Ile Val Gly Asp Ala Ile Arg Val Val Arg Arg Phe
    210                 215                 220

Ser Leu Pro Asn Val Asp Glu Gly Asp Leu Ser Asn Asn Ala Gly Val
225                 230                 235                 240

Phe Arg Phe Pro Arg Val Ser Cys Ala Ala Ala Ser Ala Asp Asp Ala
                245                 250                 255

Asp Leu Asp Pro Arg Val Ala Glu Leu Pro Pro Arg Pro Leu Leu Glu
            260                 265                 270

Ile Leu Ala Arg Glu Leu Arg Arg Leu Gly Leu Arg Leu Phe Asn
        275                 280                 285
```

```
Ile Asp Met Ile Arg Glu His Gly Thr Arg Asp Arg Phe Tyr Val Ile
    290                 295                 300

Asp Met Asn Tyr Phe Pro Gly Tyr Gly Lys Met Pro Gly Tyr Glu His
305                 310                 315                 320

Val Phe Thr Asp Phe Leu Leu Ser Leu Ala Lys Lys Glu Tyr Lys Arg
                325                 330                 335

Arg Gln Ser Tyr Ser Ser Leu Ser Ser Gly Glu Trp
            340                 345

<210> SEQ ID NO 3
<211> LENGTH: 1655
<212> TYPE: DNA
<213> ORGANISM: Zea mays
<220> FEATURE:
<221> NAME/KEY: CDS
<222> LOCATION: (246)...(1286)

<400> SEQUENCE: 3
gaattcccgg gtcgacccac gcgtccggcc attattaaca gctccgcggt ccctccctcc      60
ctcggtcggt cggcgtcggt ccctccctcc ccacccagtt agtcctcagc ctatcccgtg     120
cccgcgcaga gcaccgcctc tgctcgaccc accaccctct gtgcagagtt aattaacctt     180
gaggtttccg attgcccttc ccttccgctc ctctcgccca ttcgcggcga gattcagcgg     240 caagg atg cgc ctg cac gcg gag gtg cgg gat gag atg gag gag ggg agc    290
      Met Arg Leu His Ala Glu Val Arg Asp Glu Met Glu Glu Gly Ser
       1               5                  10                  15 gag gag ggg gct gtg acg gct tcg gcg ggg ctg tcg cca ccg cca ctc      338
Glu Glu Gly Ala Val Thr Ala Ser Ala Gly Leu Ser Pro Pro Pro Leu
             20                  25                  30 atc ggt gcg gcg gcg ccg gtt ccc cgg cta gtg gtg ggg ttc gcc ctc      386
Ile Gly Ala Ala Ala Pro Val Pro Arg Leu Val Val Gly Phe Ala Leu
         35                  40                  45 acg aag aag aag gtg aag agc ttc ctg cag ccc aag ctg ctc ctg ctg      434
Thr Lys Lys Lys Val Lys Ser Phe Leu Gln Pro Lys Leu Leu Leu Leu
     50                  55                  60 gcc agg aag aat gga atc agt ttt gta tct att gat gag tct ctt ccc      482
Ala Arg Lys Asn Gly Ile Ser Phe Val Ser Ile Asp Glu Ser Leu Pro
 65                  70                  75 ctc tca gaa caa ggc cct ttt gat gtt att tta cac aag att act agg      530
Leu Ser Glu Gln Gly Pro Phe Asp Val Ile Leu His Lys Ile Thr Arg
 80                  85                  90                  95 aag gag tgg cag aag gtt ctg gag gac tat cac gaa gaa cat cca gaa      578
Lys Glu Trp Gln Lys Val Leu Glu Asp Tyr His Glu Glu His Pro Glu
                100                 105                 110 gtt act gtc ctt gac cca cca aat gct atc gag cat ctg aac aat cga      626
Val Thr Val Leu Asp Pro Pro Asn Ala Ile Glu His Leu Asn Asn Arg
            115                 120                 125 caa tca atg ctt gaa gaa gta gct gat ttg aac ctg tca aat ttc tat      674
Gln Ser Met Leu Glu Glu Val Ala Asp Leu Asn Leu Ser Asn Phe Tyr
        130                 135                 140 gga gaa gtt tgt atc cca cgc cag ctg gtc att acg aaa gat cca tcc      722
Gly Glu Val Cys Ile Pro Arg Gln Leu Val Ile Thr Lys Asp Pro Ser
    145                 150                 155 tct ata cca act tct gta gct atg gct gga cta act ttg ccc ttg gtt      770
Ser Ile Pro Thr Ser Val Ala Met Ala Gly Leu Thr Leu Pro Leu Val
160                 165                 170                 175 gcc aag cca ttg gtt gtt gat ggg acg tct aaa ggt cat gaa cta tat      818
Ala Lys Pro Leu Val Val Asp Gly Thr Ser Lys Gly His Glu Leu Tyr
                180                 185                 190
```

-continued

```
ctt gca tat gac gag gca tcc ttg tca atg ctt gat ccg cct ctg gtt    866
Leu Ala Tyr Asp Glu Ala Ser Leu Ser Met Leu Asp Pro Pro Leu Val
        195                 200                 205 cta cag gaa ttc ata aac cat ggc ggg atc ctc ttt aag gtg tat atc    914
Leu Gln Glu Phe Ile Asn His Gly Gly Ile Leu Phe Lys Val Tyr Ile
    210                 215                 220 att ggt gaa aca ata cag gtt gtc cgc agg ttc tct ctt cct gat gtt    962
Ile Gly Glu Thr Ile Gln Val Val Arg Arg Phe Ser Leu Pro Asp Val
225                 230                 235 aac aca tat gac tta cta aac aac gtt ggc atc tat cga ttg cca aga   1010
Asn Thr Tyr Asp Leu Leu Asn Asn Val Gly Ile Tyr Arg Leu Pro Arg
240                 245                 250                 255 gtt tca tgt gct gca gct agt gcg gat gat gca gat ctt gac cct ctt   1058
Val Ser Cys Ala Ala Ala Ser Ala Asp Asp Ala Asp Leu Asp Pro Leu
                260                 265                 270 att gca gag ctt cct cca agg cca ctt cta gag aaa ctg ggc agg gag   1106
Ile Ala Glu Leu Pro Pro Arg Pro Leu Leu Glu Lys Leu Gly Arg Glu
            275                 280                 285 ctt cgt ggc cgg ctt ggt ttg aga ttg ttc aat ata gat atg att aga   1154
Leu Arg Gly Arg Leu Gly Leu Arg Leu Phe Asn Ile Asp Met Ile Arg
        290                 295                 300 gaa ctt gga acc aaa gat cgg tac tac ata att gat atc aac tac ttc   1202
Glu Leu Gly Thr Lys Asp Arg Tyr Tyr Ile Ile Asp Ile Asn Tyr Phe
    305                 310                 315 cca ggt tac ggc aaa atg cca gga tat gag cgc atg ttc aca gac ttc   1250
Pro Gly Tyr Gly Lys Met Pro Gly Tyr Glu Arg Met Phe Thr Asp Phe
320                 325                 330                 335 tta cta agt ctc gca caa gca agt aca aaa ggt act taagcgggac        1296
Leu Leu Ser Leu Ala Gln Ala Ser Thr Lys Gly Thr
                340                 345 atgaggtgca aggaagtttg tgaagaccat gctactgacg agatggcata taacggtggc  1356
aggtatgctt ccccaccgcg ccaatgtaca tttgctggag acataagcat aagcgggagg  1416
cttgaggaag ttggcaagtc tcagtgtgtg tgttcaaaat cggtggcaca tgctggactg  1476
gagtaggaaa taaccaagga aacgcttgga tgcgctgtac tcatgttgta aaatgtttaa  1536
ctgaatgaac accttcctcg tgatggctcc ctccatcgta atttggcaac catgagaatt  1596
aattctgcag cttggtaaaa aaaaaaaaaa aaaaaaaaa aaaaagggcg gccgctcta    1655

<210> SEQ ID NO 4
<211> LENGTH: 347
<212> TYPE: PRT
<213> ORGANISM: Zea mays

<400> SEQUENCE: 4

Met Arg Leu His Ala Glu Val Arg Asp Glu Met Glu Glu Gly Ser Glu
1               5                   10                  15

Glu Gly Ala Val Thr Ala Ser Ala Gly Leu Ser Pro Pro Leu Ile
            20                  25                  30

Gly Ala Ala Ala Pro Val Pro Arg Leu Val Val Gly Phe Ala Leu Thr
        35                  40                  45

Lys Lys Lys Val Lys Ser Phe Leu Gln Pro Lys Leu Leu Leu Leu Ala
    50                  55                  60

Arg Lys Asn Gly Ile Ser Phe Val Ser Ile Asp Glu Ser Leu Pro Leu
65                  70                  75                  80

Ser Glu Gln Gly Pro Phe Asp Val Ile Leu His Lys Ile Thr Arg Lys
                85                  90                  95
```

-continued

```
Glu Trp Gln Lys Val Leu Glu Asp Tyr His Glu His Pro Glu Val
            100                 105                 110

Thr Val Leu Asp Pro Pro Asn Ala Ile Glu His Leu Asn Asn Arg Gln
        115                 120                 125

Ser Met Leu Glu Glu Val Ala Asp Leu Asn Leu Ser Asn Phe Tyr Gly
    130                 135                 140

Glu Val Cys Ile Pro Arg Gln Leu Val Ile Thr Lys Asp Pro Ser Ser
145                 150                 155                 160

Ile Pro Thr Ser Val Ala Met Ala Gly Leu Thr Leu Pro Leu Val Ala
                165                 170                 175

Lys Pro Leu Val Val Asp Gly Thr Ser Lys Gly His Glu Leu Tyr Leu
            180                 185                 190

Ala Tyr Asp Glu Ala Ser Leu Ser Met Leu Asp Pro Pro Leu Val Leu
        195                 200                 205

Gln Glu Phe Ile Asn His Gly Gly Ile Leu Phe Lys Val Tyr Ile Ile
    210                 215                 220

Gly Glu Thr Ile Gln Val Val Arg Arg Phe Ser Leu Pro Asp Val Asn
225                 230                 235                 240

Thr Tyr Asp Leu Leu Asn Asn Val Gly Ile Tyr Arg Leu Pro Arg Val
                245                 250                 255

Ser Cys Ala Ala Ala Ser Ala Asp Asp Ala Asp Leu Asp Pro Leu Ile
            260                 265                 270

Ala Glu Leu Pro Pro Arg Pro Leu Leu Glu Lys Leu Gly Arg Glu Leu
        275                 280                 285

Arg Gly Arg Leu Gly Leu Arg Leu Phe Asn Ile Asp Met Ile Arg Glu
    290                 295                 300

Leu Gly Thr Lys Asp Arg Tyr Tyr Ile Ile Asp Ile Asn Tyr Phe Pro
305                 310                 315                 320

Gly Tyr Gly Lys Met Pro Gly Tyr Glu Arg Met Phe Thr Asp Phe Leu
                325                 330                 335

Leu Ser Leu Ala Gln Ala Ser Thr Lys Gly Thr
            340                 345
```

<210> SEQ ID NO 5
<211> LENGTH: 1600
<212> TYPE: DNA
<213> ORGANISM: Zea mays
<220> FEATURE:
<221> NAME/KEY: CDS
<222> LOCATION: (223)...(1278)

<400> SEQUENCE: 5

```
gcaccattat taacagctcc gcggtccctc cctccctcgg tcggtcggcg tcggtccctc      60
tccctcccca cccagttagt cctcagccta tcccgtgccc gcgcagagca ccgcctctgc     120
tcgacccacc accctctgtg cagagttaat taaccttgag gtttccgatt gcccttccct     180
tccgttcctc tcgcccattc gcggcgagat tcagcggcaa gg atg cgc ctg cac       234
                                                Met Arg Leu His
                                                  1 gcg gag gtg cgg gat gag atg gag gag ggg agc gag gtg ggg gct gtg      282
Ala Glu Val Arg Asp Glu Met Glu Glu Gly Ser Glu Val Gly Ala Val
  5              10                  15                  20 acg gct tcg gcg ggg ctg tcg cca ccg cca ctc atc ggt gcg gcg gcg      330
Thr Ala Ser Ala Gly Leu Ser Pro Pro Pro Leu Ile Gly Ala Ala Ala
            25                  30                  35 ccg gtt ccc cgg ata gtg gtg ggg ttc gcc ctc acg aag aag aag gtg      378
Pro Val Pro Arg Ile Val Val Gly Phe Ala Leu Thr Lys Lys Lys Val
```

-continued

|  | 40 | 45 | 50 |  |
|---|---|---|---|---|
| aag agc ttc ctg cag ccc aag ctg ctc ctg ctg gcc agg aag aat gga<br>Lys Ser Phe Leu Gln Pro Lys Leu Leu Leu Leu Ala Arg Lys Asn Gly<br>      55                  60              65 | | | | 426 |

```
aag agc ttc ctg cag ccc aag ctg ctc ctg ctg gcc agg aag aat gga      426
Lys Ser Phe Leu Gln Pro Lys Leu Leu Leu Leu Ala Arg Lys Asn Gly
         55                  60                  65 atc agt ttt gta tct att gat gag tct ctt ccc ctc tca gaa caa ggc      474
Ile Ser Phe Val Ser Ile Asp Glu Ser Leu Pro Leu Ser Glu Gln Gly
 70                  75                  80 cct ttt gat gtt att tta cac aag att act agg aag gag tgg cag aag      522
Pro Phe Asp Val Ile Leu His Lys Ile Thr Arg Lys Glu Trp Gln Lys
 85                  90                  95                 100 gtt ctg gag gac tat cac gaa gaa cat cca gaa gtt act gtc ctt gac      570
Val Leu Glu Asp Tyr His Glu Glu His Pro Glu Val Thr Val Leu Asp
                    105                 110                 115 cca cca aat gct atc gag cat ctg aac aat cga caa tca atg ctt gaa      618
Pro Pro Asn Ala Ile Glu His Leu Asn Asn Arg Gln Ser Met Leu Glu
                120                 125                 130 gaa gta gct gat ttg aac ctg tca aat ttc tat gga gaa gtt tgt atc      666
Glu Val Ala Asp Leu Asn Leu Ser Asn Phe Tyr Gly Glu Val Cys Ile
            135                 140                 145 cca cgc cag ctg gtc att acg aaa gat cca tcc tct ata cca act tct      714
Pro Arg Gln Leu Val Ile Thr Lys Asp Pro Ser Ser Ile Pro Thr Ser
        150                 155                 160 gta gct atg gct gga cta act ttg ccc ttg gtt gcc aag cca ttg gtt      762
Val Ala Met Ala Gly Leu Thr Leu Pro Leu Val Ala Lys Pro Leu Val
165                 170                 175                 180 gtt gat ggg acg tct aaa ggt cat gaa cta tat ctt gca tat gac gag      810
Val Asp Gly Thr Ser Lys Gly His Glu Leu Tyr Leu Ala Tyr Asp Glu
                    185                 190                 195 gca tcc ttg tca atg ctt gat ccg cct ctg gtt cta cag gaa ttc ata      858
Ala Ser Leu Ser Met Leu Asp Pro Pro Leu Val Leu Gln Glu Phe Ile
                200                 205                 210 aac cat ggc ggg atc ctc ttt aag gtg tat atc att ggt gaa aca ata      906
Asn His Gly Gly Ile Leu Phe Lys Val Tyr Ile Ile Gly Glu Thr Ile
            215                 220                 225 cag gtt gtc cgc agg ttc tct ctt cct gat gtt aac aca tat gac tta      954
Gln Val Val Arg Arg Phe Ser Leu Pro Asp Val Asn Thr Tyr Asp Leu
        230                 235                 240 cta aac aac gtt ggc atc tat cga ttg cca aga gtt tca tgt gct gca     1002
Leu Asn Asn Val Gly Ile Tyr Arg Leu Pro Arg Val Ser Cys Ala Ala
245                 250                 255                 260 gct agt gcg gat gat gca gat ctt gac cct ctt att gca gag ctt cct     1050
Ala Ser Ala Asp Asp Ala Asp Leu Asp Pro Leu Ile Ala Glu Leu Pro
                    265                 270                 275 cca agg cca ctt cta gag aaa ctg ggc agg gag ctt cgt ggc cgg ctt     1098
Pro Arg Pro Leu Leu Glu Lys Leu Gly Arg Glu Leu Arg Gly Arg Leu
                280                 285                 290 ggt ttg aga ttg ttc aat ata gat atg att aga gaa ctt gga acc aaa     1146
Gly Leu Arg Leu Phe Asn Ile Asp Met Ile Arg Glu Leu Gly Thr Lys
            295                 300                 305 gat cgg tac tac ata att gat atc aac tac ttc cca ggt tac ggc aaa     1194
Asp Arg Tyr Tyr Ile Ile Asp Ile Asn Tyr Phe Pro Gly Tyr Gly Lys
        310                 315                 320 atg cca gga tat gag cgc atg ttc aca gac ttc tta cta agt ctc gca     1242
Met Pro Gly Tyr Glu Arg Met Phe Thr Asp Phe Leu Leu Ser Leu Ala
325                 330                 335                 340 caa agc aag tac aaa agg tac tta agc ggg acg tga ggtgcaagga          1288
Gln Ser Lys Tyr Lys Arg Tyr Leu Ser Gly Thr *
                    345                 350 agtttgtgaa gaccatgcta ctgacgagat ggcatataac ggtggcagct atgcttcccc   1348
```

```
accgcgccaa tgtacatttg ctggagacat aagcataagc cggaggcttg aggaagttgg    1408
caagtctcag tgtgtgtgtt caaaatcggt ggcacatgct ggactggagt aggaaataac    1468
caaggaaacg cttggatgcg ctgtacccat gttgtaaaat gtttaactga atgaacacct    1528
tcctcgtgat ggctccctcc atcgtaattt ggcaaccatg agaattaatt ctgcaaaaaa    1588
aaaaaaaaaa aa                                                         1600
```

<210> SEQ ID NO 6
<211> LENGTH: 351
<212> TYPE: PRT
<213> ORGANISM: Zea mays

<400> SEQUENCE: 6

```
Met Arg Leu His Ala Glu Val Arg Asp Glu Met Glu Glu Gly Ser Glu
  1               5                  10                  15

Val Gly Ala Val Thr Ala Ser Ala Gly Leu Ser Pro Pro Pro Leu Ile
             20                  25                  30

Gly Ala Ala Pro Val Pro Arg Ile Val Val Gly Phe Ala Leu Thr
         35                  40                  45

Lys Lys Lys Val Lys Ser Phe Leu Gln Pro Lys Leu Leu Leu Ala
 50                  55                  60

Arg Lys Asn Gly Ile Ser Phe Val Ser Ile Asp Glu Ser Leu Pro Leu
 65                  70                  75                  80

Ser Glu Gln Gly Pro Phe Asp Val Ile Leu His Lys Ile Thr Arg Lys
                 85                  90                  95

Glu Trp Gln Lys Val Leu Glu Asp Tyr His Glu His Pro Glu Val
            100                 105                 110

Thr Val Leu Asp Pro Pro Asn Ala Ile Glu His Leu Asn Asn Arg Gln
            115                 120                 125

Ser Met Leu Glu Glu Val Ala Asp Leu Asn Leu Ser Asn Phe Tyr Gly
        130                 135                 140

Glu Val Cys Ile Pro Arg Gln Leu Val Ile Thr Lys Asp Pro Ser Ser
145                 150                 155                 160

Ile Pro Thr Ser Val Ala Met Ala Gly Leu Thr Leu Pro Leu Val Ala
                165                 170                 175

Lys Pro Leu Val Val Asp Gly Thr Ser Lys Gly His Glu Leu Tyr Leu
            180                 185                 190

Ala Tyr Asp Glu Ala Ser Leu Ser Met Leu Asp Pro Pro Leu Val Leu
        195                 200                 205

Gln Glu Phe Ile Asn His Gly Gly Ile Leu Phe Lys Val Tyr Ile Ile
    210                 215                 220

Gly Glu Thr Ile Gln Val Val Arg Arg Phe Ser Leu Pro Asp Val Asn
225                 230                 235                 240

Thr Tyr Asp Leu Leu Asn Asn Val Gly Ile Tyr Arg Leu Pro Arg Val
                245                 250                 255

Ser Cys Ala Ala Ala Ser Ala Asp Asp Ala Asp Leu Asp Pro Leu Ile
            260                 265                 270

Ala Glu Leu Pro Pro Arg Pro Leu Leu Glu Lys Leu Gly Arg Glu Leu
        275                 280                 285

Arg Gly Arg Leu Gly Leu Arg Leu Phe Asn Ile Asp Met Ile Arg Glu
    290                 295                 300

Leu Gly Thr Lys Asp Arg Tyr Tyr Ile Ile Asp Ile Asn Tyr Phe Pro
305                 310                 315                 320
```

```
Gly Tyr Gly Lys Met Pro Gly Tyr Glu Arg Met Phe Thr Asp Phe Leu
            325                 330                 335
Leu Ser Leu Ala Gln Ser Lys Tyr Lys Arg Tyr Leu Ser Gly Thr
        340                 345                 350

<210> SEQ ID NO 7
<211> LENGTH: 1428
<212> TYPE: DNA
<213> ORGANISM: Zea mays
<220> FEATURE:
<221> NAME/KEY: CDS
<222> LOCATION: (56)...(1084)

<400> SEQUENCE: 7
ccacgcgtcc gcaaatttca atctccatcg atcgattcct cccgaacccg acccg atg      58
                                                             Met
                                                               1 gcc tcc gac gcc gcc gcc gag ccc tcc tcc ggc gtc acc cac ccc ccg     106
Ala Ser Asp Ala Ala Ala Glu Pro Ser Ser Gly Val Thr His Pro Pro
          5                  10                  15 cgc tac gtc atc ggt tac gcg ctc gcg ccg aag aag cag caa agc ttc     154
Arg Tyr Val Ile Gly Tyr Ala Leu Ala Pro Lys Lys Gln Gln Ser Phe
     20                  25                  30 atc cag ccg tcg ctg gtg gcc cag gcg gcg tcg cgg ggc atg gac ctc     202
Ile Gln Pro Ser Leu Val Ala Gln Ala Ala Ser Arg Gly Met Asp Leu
 35                  40                  45 gtc ccc gtg gat gcg tcg cag ccc ctg gca gag caa ggg ccc ttc cac     250
Val Pro Val Asp Ala Ser Gln Pro Leu Ala Glu Gln Gly Pro Phe His
 50                  55                  60                  65 ctc ctc atc cac aag ctc tac gga gac gac tgg cgc gcc cag ctc gtg     298
Leu Leu Ile His Lys Leu Tyr Gly Asp Asp Trp Arg Ala Gln Leu Val
             70                  75                  80 gcc ttc gcc gcg cgc cac ccg gcc gtc ccc atc gtc gac ccg ccc cac     346
Ala Phe Ala Ala Arg His Pro Ala Val Pro Ile Val Asp Pro Pro His
         85                  90                  95 gcc atc gac cgc ctc cac aac cgc atc tcc atg ctc cag gtc gtc tcc     394
Ala Ile Asp Arg Leu His Asn Arg Ile Ser Met Leu Gln Val Val Ser
    100                 105                 110 gag ctc gac cac gcc gcc gac cag gac agc act ttc ggt atc ccc agc     442
Glu Leu Asp His Ala Ala Asp Gln Asp Ser Thr Phe Gly Ile Pro Ser
115                 120                 125 cag gtc gtc gtc tac gac gct gcc gcg ctc gcc gac ttc gga ctc ctt     490
Gln Val Val Val Tyr Asp Ala Ala Ala Leu Ala Asp Phe Gly Leu Leu
130                 135                 140                 145 gcc gcg ctc cgc ttc ccg ctc atc gcc aag ccc ctc gtc gcc gac ggc     538
Ala Ala Leu Arg Phe Pro Leu Ile Ala Lys Pro Leu Val Ala Asp Gly
            150                 155                 160 acc gcc aag tcc cac aag atg tcg ctc gtc tac cac cgc gag ggc ctc     586
Thr Ala Lys Ser His Lys Met Ser Leu Val Tyr His Arg Glu Gly Leu
        165                 170                 175 ggc aag ctc cgc ccg ccg ctt gtg ctc cag gag ttc gtc aac cat ggc     634
Gly Lys Leu Arg Pro Pro Leu Val Leu Gln Glu Phe Val Asn His Gly
    180                 185                 190 ggc gtc atc ttc aag gtc tac gtc gtc ggc ggc cac gtc act tgc gtc     682
Gly Val Ile Phe Lys Val Tyr Val Val Gly Gly His Val Thr Cys Val
195                 200                 205 aag cgc cgt agc ctg ccc gac gtg tcc ccc gag gat gac gca tcg gcc     730
Lys Arg Arg Ser Leu Pro Asp Val Ser Pro Glu Asp Asp Ala Ser Ala
210                 215                 220                 225 cag gga tcc gtc tcc ttc tcc cag gtc tcc aac ctc ccc act gag cgc     778
Gln Gly Ser Val Ser Phe Ser Gln Val Ser Asn Leu Pro Thr Glu Arg
```

-continued

```
                      230                 235                 240
acg gcg gag gag tac tac ggc gaa aag agt ctc gag gac gcc gtc gtg       826
Thr Ala Glu Glu Tyr Tyr Gly Glu Lys Ser Leu Glu Asp Ala Val Val
                      245                 250                 255 ccg ccc gcc gca ttc atc aac cag atc gcg ggc ggc ctc cgc cgc gcg       874
Pro Pro Ala Ala Phe Ile Asn Gln Ile Ala Gly Gly Leu Arg Arg Ala
                260                 265                 270 ctg ggc ctg caa ctc ttc aac ttc gac atg atc cgc gac gtc cgc gcc       922
Leu Gly Leu Gln Leu Phe Asn Phe Asp Met Ile Arg Asp Val Arg Ala
            275                 280                 285 ggc gac cgc tat ctc gtc att gac atc aac tac ttc ccg ggc tac gcc       970
Gly Asp Arg Tyr Leu Val Ile Asp Ile Asn Tyr Phe Pro Gly Tyr Ala
290                 295                 300                 305 aag atg cca gga tac gag act gtc ctc acg gat ttc ttc tgg gag atg      1018
Lys Met Pro Gly Tyr Glu Thr Val Leu Thr Asp Phe Phe Trp Glu Met
                    310                 315                 320 gtc cat aag gac ggc gtg ggc aac caa cag gag gag aaa ggg gcc aac      1066
Val His Lys Asp Gly Val Gly Asn Gln Gln Glu Glu Lys Gly Ala Asn
                325                 330                 335 cat gtt gtc gtg aaa taa gatgatgatt gatggcactg gatatctggc             1114
His Val Val Val Lys *
            340 gaatgctgct gattctggat gcagaattcg atgaggggat ttagttggtt gtagtatctg    1174 gcgaatgctg ctggttctgg atgcagaatt tgatgagggg atttagttgg atttcaaccc    1234 atagcatgcc gaggacctcc tagctctttc caaaccagtt gtttaggtat cttttctggg    1294 taagtcagct tcatctagtt tagtctgtct gaacaaaaga gtgggacatg acccaaacgg    1354 aattctaatg aaaacgagc tctctatctg caaaaaaaaa aaaaaaaaaa aaaaaaaaaa     1414 aaaaaaaaaa aaaa                                                     1428

<210> SEQ ID NO 8
<211> LENGTH: 342
<212> TYPE: PRT
<213> ORGANISM: Zea mays

<400> SEQUENCE: 8

Met Ala Ser Asp Ala Ala Ala Glu Pro Ser Gly Val Thr His Pro
1               5                   10                  15

Pro Arg Tyr Val Ile Gly Tyr Ala Leu Ala Pro Lys Lys Gln Gln Ser
                20                  25                  30

Phe Ile Gln Pro Ser Leu Val Ala Gln Ala Ala Ser Arg Gly Met Asp
            35                  40                  45

Leu Val Pro Val Asp Ala Ser Gln Pro Leu Ala Glu Gln Gly Pro Phe
        50                  55                  60

His Leu Leu Ile His Lys Leu Tyr Gly Asp Asp Trp Arg Ala Gln Leu
65                  70                  75                  80

Val Ala Phe Ala Ala Arg His Pro Ala Val Pro Ile Val Asp Pro Pro
                85                  90                  95

His Ala Ile Asp Arg Leu His Asn Arg Ile Ser Met Leu Gln Val Val
            100                 105                 110

Ser Glu Leu Asp His Ala Ala Asp Gln Asp Ser Thr Phe Gly Ile Pro
        115                 120                 125

Ser Gln Val Val Val Tyr Asp Ala Ala Ala Leu Ala Asp Phe Gly Leu
    130                 135                 140

Leu Ala Ala Leu Arg Phe Pro Leu Ile Ala Lys Pro Leu Val Ala Asp
145                 150                 155                 160
```

-continued

```
Gly Thr Ala Lys Ser His Lys Met Ser Leu Val Tyr His Arg Glu Gly
            165                 170                 175
Leu Gly Lys Leu Arg Pro Pro Leu Val Leu Gln Glu Phe Val Asn His
        180                 185                 190
Gly Gly Val Ile Phe Lys Val Tyr Val Gly Gly His Val Thr Cys
    195                 200                 205
Val Lys Arg Arg Ser Leu Pro Asp Val Ser Pro Glu Asp Ala Ser
    210                 215                 220
Ala Gln Gly Ser Val Ser Phe Ser Gln Val Ser Asn Leu Pro Thr Glu
225                 230                 235                 240
Arg Thr Ala Glu Glu Tyr Tyr Gly Glu Lys Ser Leu Glu Asp Ala Val
            245                 250                 255
Val Pro Pro Ala Ala Phe Ile Asn Gln Ile Ala Gly Gly Leu Arg Arg
        260                 265                 270
Ala Leu Gly Leu Gln Leu Phe Asn Phe Asp Met Ile Arg Asp Val Arg
    275                 280                 285
Ala Gly Asp Arg Tyr Leu Val Ile Asp Ile Asn Tyr Phe Pro Gly Tyr
290                 295                 300
Ala Lys Met Pro Gly Tyr Glu Thr Val Leu Thr Asp Phe Phe Trp Glu
305                 310                 315                 320
Met Val His Lys Asp Gly Val Gly Asn Gln Gln Glu Glu Lys Gly Ala
            325                 330                 335
Asn His Val Val Val Lys
            340
```

<210> SEQ ID NO 9
<211> LENGTH: 1295
<212> TYPE: DNA
<213> ORGANISM: Zea mays
<220> FEATURE:
<221> NAME/KEY: CDS
<222> LOCATION: (19)...(1143)

<400> SEQUENCE: 9

```
cgatagtcca ccaagtca atg gcg gcg gag cag tgc cag tcc tca ggc ggc        51
                    Met Ala Ala Glu Gln Cys Gln Ser Ser Gly Gly
                     1               5                   10 agc tcg ccg cgg cct cgc gcc gca tac acc atc ggc tac gcg atg ctg        99
Ser Ser Pro Arg Pro Arg Ala Ala Tyr Thr Ile Gly Tyr Ala Met Leu
         15                  20                  25 ccc aac aag cac gat acc ttc gtc cag ccg tcg ttc atc gac ctg gca       147
Pro Asn Lys His Asp Thr Phe Val Gln Pro Ser Phe Ile Asp Leu Ala
     30                  35                  40 gcg cag cac ggc atc cgg ctc gtg gcg ctc gac gcc tcc agg ccg ctc       195
Ala Gln His Gly Ile Arg Leu Val Ala Leu Asp Ala Ser Arg Pro Leu
 45                  50                  55 gcg gag cag ggc ccc cag ctg gac ctc gtc gtg cac aag ctg tac ggc       243
Ala Glu Gln Gly Pro Gln Leu Asp Leu Val Val His Lys Leu Tyr Gly
 60                  65                  70                  75 cag gcg tgg cgc gcg cgg ctg gag gcc ttc tcg gcg ctc cac ccg gac       291
Gln Ala Trp Arg Ala Arg Leu Glu Ala Phe Ser Ala Leu His Pro Asp
             80                  85                  90 gtc cca atc atc gac ccg ccc gcc gcc atc gac cgc atc ctg gac cgc       339
Val Pro Ile Ile Asp Pro Pro Ala Ala Ile Asp Arg Ile Leu Asp Arg
         95                  100                 105 ttc acc atg ctg gac gtc gtc tcg ggg ctc gac tgc gtg gcc gtg ccc       387
Phe Thr Met Leu Asp Val Val Ser Gly Leu Asp Cys Val Ala Val Pro
     110                 115                 120
```

```
agg cag gtc atg gtc cac gac gcc ggg gcc ctg cag cag gcc gcc gac    435
Arg Gln Val Met Val His Asp Ala Gly Ala Leu Gln Gln Ala Ala Asp
    125                 130                 135 gcc gcc gcc gac gac gtg ctc ggc ctc ggc ggc ctc cgg ttc ccg ctc    483
Ala Ala Ala Asp Asp Val Leu Gly Leu Gly Gly Leu Arg Phe Pro Leu
140                 145                 150                 155 gtc gcc aag ccc gtg gag gtg gac ggc agc gcg gcg tcg cac gac ctc    531
Val Ala Lys Pro Val Glu Val Asp Gly Ser Ala Ala Ser His Asp Leu
                160                 165                 170 tgc ctg gtg tac cgc cgc gag ggc ctg cgc ggc ctg cgc ggc cgc ccg    579
Cys Leu Val Tyr Arg Arg Glu Gly Leu Arg Gly Leu Arg Gly Arg Pro
            175                 180                 185 ccg ctc gtg ctg cag gag ttc gcc aac cac ggc ggc gtg ctc ttc aag    627
Pro Leu Val Leu Gln Glu Phe Ala Asn His Gly Gly Val Leu Phe Lys
        190                 195                 200 gtg tac gtg gtg ggc gac cgc gcc acg tgc gtg gtg cgg agc agc ctg    675
Val Tyr Val Val Gly Asp Arg Ala Thr Cys Val Val Arg Ser Ser Leu
    205                 210                 215 ccg gac gtg ccg ccg gag cgc ctc cgg gac ccc gcc gcc gcc gcc gcg    723
Pro Asp Val Pro Pro Glu Arg Leu Arg Asp Pro Ala Ala Ala Ala Ala
220                 225                 230                 235 gcc ccc ttc gcc aac atc tcc ctc ctc gcc ccc agc ggc ggc gac gag    771
Ala Pro Phe Ala Asn Ile Ser Leu Leu Ala Pro Ser Gly Gly Asp Glu
                240                 245                 250 ggc tcc gag aag gtg gta ccg ccg ccc cag gac ttc gtc gac agg gtc    819
Gly Ser Glu Lys Val Val Pro Pro Pro Gln Asp Phe Val Asp Arg Val
            255                 260                 265 gcc cgc gag atc cgg cgg gca gtg ggc ctg cac ctc atc aac ttc gac    867
Ala Arg Glu Ile Arg Arg Ala Val Gly Leu His Leu Ile Asn Phe Asp
        270                 275                 280 ctc atc cgg acg agg gac gac gct gca ggc ggc gac gcc aat aag tac    915
Leu Ile Arg Thr Arg Asp Asp Ala Ala Gly Gly Asp Ala Asn Lys Tyr
    285                 290                 295 ctc gtc ctc gac atc aac tac tgc ccg ggc tac tcc aaa atg ccc ggc    963
Leu Val Leu Asp Ile Asn Tyr Cys Pro Gly Tyr Ser Lys Met Pro Gly
300                 305                 310                 315 ttt gag cct gtc ctc act gaa ttc ttc ctg gag agg ctt cgc tct cgc    1011
Phe Glu Pro Val Leu Thr Glu Phe Phe Leu Glu Arg Leu Arg Ser Arg
                320                 325                 330 agc aga agc atc gat gag cgg cct gcc ccg ggg gcg gag gcg agg cag    1059
Ser Arg Ser Ile Asp Glu Arg Pro Ala Pro Gly Ala Glu Ala Arg Gln
            335                 340                 345 gca gag gca gag gca gag gcc gag ccc agc agc gcc acc atc ccc atc    1107
Ala Glu Ala Glu Ala Glu Ala Glu Pro Ser Ser Ala Thr Ile Pro Ile
        350                 355                 360 ccg ccg gga gcg gag gcg agg ctg gct cag gcc taa attcgccagg        1153
Pro Pro Gly Ala Glu Ala Arg Leu Ala Gln Ala *
    365                 370 ttcctcacat catccagttt gtttaatttg gaccatatac accagtgaag cgtgaagtga  1213
agccgccttg attctaacct ttcattgcaa agggaattaa ataaacacca gttgctttgt  1273
acccaaaaaa aaaaaaaaaa aa                                           1295

<210> SEQ ID NO 10
<211> LENGTH: 374
<212> TYPE: PRT
<213> ORGANISM: Zea mays

<400> SEQUENCE: 10
```

```
Met Ala Ala Glu Gln Cys Gln Ser Ser Gly Gly Ser Ser Pro Arg Pro
  1               5                  10                  15

Arg Ala Ala Tyr Thr Ile Gly Tyr Ala Met Leu Pro Asn Lys His Asp
             20                  25                  30

Thr Phe Val Gln Pro Ser Phe Ile Asp Leu Ala Ala Gln His Gly Ile
         35                  40                  45

Arg Leu Val Ala Leu Asp Ala Ser Arg Pro Leu Ala Glu Gln Gly Pro
 50                  55                  60

Gln Leu Asp Leu Val His Lys Leu Tyr Gly Gln Ala Trp Arg Ala
 65                  70                  75                  80

Arg Leu Glu Ala Phe Ser Ala Leu His Pro Asp Val Pro Ile Ile Asp
                 85                  90                  95

Pro Pro Ala Ala Ile Asp Arg Ile Leu Asp Arg Phe Thr Met Leu Asp
            100                 105                 110

Val Val Ser Gly Leu Asp Cys Val Ala Val Pro Arg Gln Val Met Val
            115                 120                 125

His Asp Ala Gly Ala Leu Gln Gln Ala Ala Asp Ala Ala Asp Asp
    130                 135                 140

Val Leu Gly Leu Gly Gly Leu Arg Phe Pro Leu Val Ala Lys Pro Val
145                 150                 155                 160

Glu Val Asp Gly Ser Ala Ala Ser His Asp Leu Cys Leu Val Tyr Arg
                165                 170                 175

Arg Glu Gly Leu Arg Gly Leu Arg Gly Arg Pro Pro Leu Val Leu Gln
            180                 185                 190

Glu Phe Ala Asn His Gly Gly Val Leu Phe Lys Val Tyr Val Val Gly
        195                 200                 205

Asp Arg Ala Thr Cys Val Val Arg Ser Ser Leu Pro Asp Val Pro Pro
    210                 215                 220

Glu Arg Leu Arg Asp Pro Ala Ala Ala Ala Ala Pro Phe Ala Asn
225                 230                 235                 240

Ile Ser Leu Leu Ala Pro Ser Gly Gly Asp Glu Gly Ser Glu Lys Val
                245                 250                 255

Val Pro Pro Pro Gln Asp Phe Val Asp Arg Val Ala Arg Glu Ile Arg
            260                 265                 270

Arg Ala Val Gly Leu His Leu Ile Asn Phe Asp Leu Ile Arg Thr Arg
        275                 280                 285

Asp Asp Ala Ala Gly Gly Asp Ala Asn Lys Tyr Leu Val Leu Asp Ile
    290                 295                 300

Asn Tyr Cys Pro Gly Tyr Ser Lys Met Pro Gly Phe Glu Pro Val Leu
305                 310                 315                 320

Thr Glu Phe Phe Leu Gly Arg Leu Arg Ser Arg Ser Arg Ser Ile Asp
                325                 330                 335

Glu Arg Pro Ala Pro Gly Ala Glu Ala Arg Gln Ala Glu Ala Glu Ala
            340                 345                 350

Glu Ala Glu Pro Ser Ser Ala Thr Ile Pro Ile Pro Pro Gly Ala Glu
        355                 360                 365

Ala Arg Leu Ala Gln Ala
        370

<210> SEQ ID NO 11
<211> LENGTH: 1837
<212> TYPE: DNA
<213> ORGANISM: Zea mays
<220> FEATURE:
<221> NAME/KEY: CDS
```

<220> FEATURE:
<221> NAME/KEY: misc_feature
<222> LOCATION: (1)...(1837)
<223> OTHER INFORMATION: n = A,T,C or G

<400> SEQUENCE: 11

```
gggcgttcgg cccggcagcc cccaagtccc atcgccgagc agaaagtcag gaacagaact      60
caggcgttgg cgattggcat ctccctcccc taagcc atg gct acc ggg cgg ccc       114
                                        Met Ala Thr Gly Arg Pro
                                          1               5 gta cga ctc gtg ctg gat gcc tcc ctc ctc ctc gac ccc tcc tcc acc       162
Val Arg Leu Val Leu Asp Ala Ser Leu Leu Leu Asp Pro Ser Ser Thr
         10                  15                  20 agg gag gcg gcg gcg gtg gcg ctg cgg ncc ggg gta gag gag ttg ctg       210
Arg Glu Ala Ala Ala Val Ala Leu Arg Xaa Gly Val Glu Glu Leu Leu
             25                  30                  35 cgg cgg ttg cgc tac tcc aac ctg agc gtg gca atc tgc tat gca gag       258
Arg Arg Leu Arg Tyr Ser Asn Leu Ser Val Ala Ile Cys Tyr Ala Glu
     40                  45                  50 ggc atg cca act aat gag tca gac ttt ctt gaa aag gtc gca agc tca       306
Gly Met Pro Thr Asn Glu Ser Asp Phe Leu Glu Lys Val Ala Ser Ser
 55                  60                  65                  70 cac ttg ttt gga tct ata gta ctt ctt gca aaa agt ggg aat ctt tct       354
His Leu Phe Gly Ser Ile Val Leu Leu Ala Lys Ser Gly Asn Leu Ser
                 75                  80                  85 cca att gaa tta atg ata gaa tgg agc cga aca agt ttt tgt ttt tat       402
Pro Ile Glu Leu Met Ile Glu Trp Ser Arg Thr Ser Phe Cys Phe Tyr
             90                  95                 100 gcg act tca aga gtt gac aaa ggt tta att tct gag ctc cag aat cag       450
Ala Thr Ser Arg Val Asp Lys Gly Leu Ile Ser Glu Leu Gln Asn Gln
        105                 110                 115 aac tgg aga gtt ctt tct gta gct aat gaa tgt agc ata gag gtt cct       498
Asn Trp Arg Val Leu Ser Val Ala Asn Glu Cys Ser Ile Glu Val Pro
    120                 125                 130 ggt gtt tta aat gtt caa agg ctt cag gag ttg ctt ctc acc ttg gct       546
Gly Val Leu Asn Val Gln Arg Leu Gln Glu Leu Leu Leu Thr Leu Ala
135                 140                 145                 150 act cta atg aaa aag gaa ctt tgt ggc tca tct gtt ctg gtg att gga       594
Thr Leu Met Lys Lys Glu Leu Cys Gly Ser Ser Val Leu Val Ile Gly
                155                 160                 165 tat ata atg aaa aaa tcc cgt gag gaa gac ttc gca aag gca act tct       642
Tyr Ile Met Lys Lys Ser Arg Glu Glu Asp Phe Ala Lys Ala Thr Ser
            170                 175                 180 tta gaa gga gca ttt ccc ata tat cct agt aag ggc agt ctt atc ttt       690
Leu Glu Gly Ala Phe Pro Ile Tyr Pro Ser Lys Gly Ser Leu Ile Phe
        185                 190                 195 gtt ccc ctc tct ttc gaa att cca tta agt ttg caa ctg caa gaa gtt       738
Val Pro Leu Ser Phe Glu Ile Pro Leu Ser Leu Gln Leu Gln Glu Val
    200                 205                 210 gat atg gtc ctc cac aaa ata act gat gag att gtc aag atc gat cca       786
Asp Met Val Leu His Lys Ile Thr Asp Glu Ile Val Lys Ile Asp Pro
215                 220                 225                 230 aac tgc tcc att gat ttt cca aaa ggg att tca ttt tct gca gga atg       834
Asn Cys Ser Ile Asp Phe Pro Lys Gly Ile Ser Phe Ser Ala Gly Met
                235                 240                 245 tct gaa att ata aga ttt gtg gaa gag cac cct gat ttt tgt atc atg       882
Ser Glu Ile Ile Arg Phe Val Glu Glu His Pro Asp Phe Cys Ile Met
            250                 255                 260 gac cca ttt aaa aac att tac cca ttg ctt gac cgt ctt caa atc caa       930
Asp Pro Phe Lys Asn Ile Tyr Pro Leu Leu Asp Arg Leu Gln Ile Gln
```

```
                Asp Pro Phe Lys Asn Ile Tyr Pro Leu Leu Asp Arg Leu Gln Ile Gln
                    265                 270                 275 aaa atc ctt gtc cgg ttg caa gaa ctt ggc act gaa gga aag cca aaa             978
Lys Ile Leu Val Arg Leu Gln Glu Leu Gly Thr Glu Gly Lys Pro Lys
            280                 285                 290 ctt cga gca ccg tat tct tgc aag gtt gac agt ttt cat aat ggt gaa            1026
Leu Arg Ala Pro Tyr Ser Cys Lys Val Asp Ser Phe His Asn Gly Glu
295                 300                 305                 310 ttg gat aag cat cta gta gaa gct aat tta tcc ttc cca ctc att gtg            1074
Leu Asp Lys His Leu Val Glu Ala Asn Leu Ser Phe Pro Leu Ile Val
                315                 320                 325 aag cca caa gtc gct tgt gga gtc gct gat gcc cac aat atg gca ctg            1122
Lys Pro Gln Val Ala Cys Gly Val Ala Asp Ala His Asn Met Ala Leu
            330                 335                 340 gtt ttt cag att gaa gaa ttt agc aac ctc agt gtg ccc ctt cct gct            1170
Val Phe Gln Ile Glu Glu Phe Ser Asn Leu Ser Val Pro Leu Pro Ala
        345                 350                 355 gtg cta cag gaa tac gtg gat cac gga tcc aag att ttc aag ttc tat            1218
Val Leu Gln Glu Tyr Val Asp His Gly Ser Lys Ile Phe Lys Phe Tyr
    360                 365                 370 gtg atc gga gac aag gtt ttc tac gcc gtt aga gac tca atg ccc aac            1266
Val Ile Gly Asp Lys Val Phe Tyr Ala Val Arg Asp Ser Met Pro Asn
375                 380                 385                 390 gcg cgc ttc ctg aag ccg tcg tca gga ggt gaa gct ctt aca ttt aat            1314
Ala Arg Phe Leu Lys Pro Ser Ser Gly Gly Glu Ala Leu Thr Phe Asn
                395                 400                 405 agt ttg aag act ctt ccg gtg gct acg aat gag cag cga ccg cag acc            1362
Ser Leu Lys Thr Leu Pro Val Ala Thr Asn Glu Gln Arg Pro Gln Thr
            410                 415                 420 ggc gcg gaa gat ggc aag ctg tta gat gcc gat ctg gta gaa gag gcc            1410
Gly Ala Glu Asp Gly Lys Leu Leu Asp Ala Asp Leu Val Glu Glu Ala
        425                 430                 435 gca aaa ttc ctg aag ggg ctg ctt ggg ctt aca gta ttt gga ttc gat            1458
Ala Lys Phe Leu Lys Gly Leu Leu Gly Leu Thr Val Phe Gly Phe Asp
    440                 445                 450 gtc gtc gtc caa gaa ggc acc gga gac cat gtc ata gtg gac ctg aac            1506
Val Val Val Gln Glu Gly Thr Gly Asp His Val Ile Val Asp Leu Asn
455                 460                 465                 470 tac ctg ccg tcg ttc aaa gag gtt ccc gac tcg gag gcg gtg cct gcg            1554
Tyr Leu Pro Ser Phe Lys Glu Val Pro Asp Ser Glu Ala Val Pro Ala
                475                 480                 485 ttc tgg gac gcg gtc agg cag gcg tac gag tcg acg cgc ggg aat gcg            1602
Phe Trp Asp Ala Val Arg Gln Ala Tyr Glu Ser Thr Arg Gly Asn Ala
            490                 495                 500 aat gcc cag ggt taa taaggtgtca aggctcttcc cgaataagtg aatctacgtg            1657
Asn Ala Gln Gly *
        505 gagtggagcg cagcagagag aggagagccg cagtggttgt aatggttctg gagcagactc          1717 ggagtaatgt tcggctgtag ctgtgggaat aagcgaaatc gggagcggaa taataattaa          1777 caacaatccg ccatgtttag ctgtccaaaa aaaaaaaaaa aaaaaaaaaa aaaaaaaaaa          1837

<210> SEQ ID NO 12
<211> LENGTH: 506
<212> TYPE: PRT
<213> ORGANISM: Zea mays
<220> FEATURE:
<221> NAME/KEY: UNSURE
<222> LOCATION: (1)...(506)
<223> OTHER INFORMATION: Xaa= any amino acid
```

<400> SEQUENCE: 12

```
Met Ala Thr Gly Arg Pro Val Arg Leu Val Leu Asp Ala Ser Leu Leu
  1               5                  10                  15

Leu Asp Pro Ser Ser Thr Arg Glu Ala Ala Val Ala Leu Arg Xaa
             20                  25                  30

Gly Val Glu Glu Leu Leu Arg Arg Leu Arg Tyr Ser Asn Leu Ser Val
             35                  40                  45

Ala Ile Cys Tyr Ala Glu Gly Met Pro Thr Asn Glu Ser Asp Phe Leu
 50                  55                  60

Glu Lys Val Ala Ser Ser His Leu Phe Gly Ser Ile Val Leu Leu Ala
 65                  70                  75                  80

Lys Ser Gly Asn Leu Ser Pro Ile Glu Leu Met Ile Glu Trp Ser Arg
                 85                  90                  95

Thr Ser Phe Cys Phe Tyr Ala Thr Ser Arg Val Asp Lys Gly Leu Ile
                100                 105                 110

Ser Glu Leu Gln Asn Gln Asn Trp Arg Val Leu Ser Val Ala Asn Glu
            115                 120                 125

Cys Ser Ile Glu Val Pro Gly Val Leu Asn Val Gln Arg Leu Gln Glu
130                 135                 140

Leu Leu Leu Thr Leu Ala Thr Leu Met Lys Lys Glu Leu Cys Gly Ser
145                 150                 155                 160

Ser Val Leu Val Ile Gly Tyr Ile Met Lys Lys Ser Arg Glu Glu Asp
                165                 170                 175

Phe Ala Lys Ala Thr Ser Leu Glu Gly Ala Phe Pro Ile Tyr Pro Ser
            180                 185                 190

Lys Gly Ser Leu Ile Phe Val Pro Leu Ser Phe Glu Ile Pro Leu Ser
            195                 200                 205

Leu Gln Leu Gln Glu Val Asp Met Val Leu His Lys Ile Thr Asp Glu
210                 215                 220

Ile Val Lys Ile Asp Pro Asn Cys Ser Ile Asp Phe Pro Lys Gly Ile
225                 230                 235                 240

Ser Phe Ser Ala Gly Met Ser Glu Ile Ile Arg Phe Val Glu Glu His
                245                 250                 255

Pro Asp Phe Cys Ile Met Asp Pro Phe Lys Asn Ile Tyr Pro Leu Leu
            260                 265                 270

Asp Arg Leu Gln Ile Gln Lys Ile Leu Val Arg Leu Gln Glu Leu Gly
            275                 280                 285

Thr Glu Gly Lys Pro Lys Leu Arg Ala Pro Tyr Ser Cys Lys Val Asp
            290                 295                 300

Ser Phe His Asn Gly Glu Leu Asp Lys His Leu Val Glu Ala Asn Leu
305                 310                 315                 320

Ser Phe Pro Leu Ile Val Lys Pro Gln Val Ala Cys Gly Val Ala Asp
                325                 330                 335

Ala His Asn Met Ala Leu Val Phe Gln Ile Glu Glu Phe Ser Asn Leu
            340                 345                 350

Ser Val Pro Leu Pro Ala Val Leu Gln Glu Tyr Val Asp His Gly Ser
            355                 360                 365

Lys Ile Phe Lys Phe Tyr Val Ile Gly Asp Lys Val Phe Tyr Ala Val
            370                 375                 380

Arg Asp Ser Met Pro Asn Ala Arg Phe Leu Lys Pro Ser Ser Gly Gly
385                 390                 395                 400

Glu Ala Leu Thr Phe Asn Ser Leu Lys Thr Leu Pro Val Ala Thr Asn
                405                 410                 415
```

```
Glu Gln Arg Pro Gln Thr Gly Ala Glu Asp Gly Lys Leu Leu Asp Ala
            420                 425                 430

Asp Leu Val Glu Ala Ala Lys Phe Leu Lys Gly Leu Leu Gly Leu
        435                 440                 445

Thr Val Phe Gly Phe Asp Val Val Gln Glu Gly Thr Gly Asp His
    450                 455                 460

Val Ile Val Asp Leu Asn Tyr Leu Pro Ser Phe Lys Glu Val Pro Asp
465                 470                 475                 480

Ser Glu Ala Val Pro Ala Phe Trp Asp Ala Val Arg Gln Ala Tyr Glu
                485                 490                 495

Ser Thr Arg Gly Asn Ala Asn Ala Gln Gly
            500                 505

<210> SEQ ID NO 13
<211> LENGTH: 1808
<212> TYPE: DNA
<213> ORGANISM: Zea mays
<220> FEATURE:
<221> NAME/KEY: CDS
<222> LOCATION: (72)...(1580)

<400> SEQUENCE: 13
gaattcggca cgagcagaaa gccaggaaca gaactcaggc gttggcgatt ggcatctccc      60
tcccctaagc c atg gct acc ggg cgg ccc gta cga ctc gtg ctg gat gcc     110
             Met Ala Thr Gly Arg Pro Val Arg Leu Val Leu Asp Ala
                   1               5                  10 tcc ctc ctc ctc gac ccc tcc tcc acc agg gag gcg gcg gcg gtg gcg     158
Ser Leu Leu Leu Asp Pro Ser Ser Thr Arg Glu Ala Ala Ala Val Ala
     15                  20                  25 ctg cgg ccc ggg gta gag gag ctg ctg cgg cgg ttg cgc tac tcc aac     206
Leu Arg Pro Gly Val Glu Glu Leu Leu Arg Arg Leu Arg Tyr Ser Asn
 30                  35                  40                  45 ctg aac gtg gca atc tgc tat gca gag ggc atg cca aat aat gag tca     254
Leu Asn Val Ala Ile Cys Tyr Ala Glu Gly Met Pro Asn Asn Glu Ser
                 50                  55                  60 ggc ttt ctt gaa aag gtc gca agc tca cac ttg ttt ggc tct att gca     302
Gly Phe Leu Glu Lys Val Ala Ser Ser His Leu Phe Gly Ser Ile Ala
             65                  70                  75 ctt ctt gcg aaa agc ggg aat ctt tct cta act gaa tta atg tta gaa     350
Leu Leu Ala Lys Ser Gly Asn Leu Ser Leu Thr Glu Leu Met Leu Glu
         80                  85                  90 tgg agc cga aca agt ttt tgt ttt tat gcg acg tca aga gtt gac aaa     398
Trp Ser Arg Thr Ser Phe Cys Phe Tyr Ala Thr Ser Arg Val Asp Lys
 95                 100                 105 ggt tta att tct gag ctc cag aat cag aac tgg aga gtt ctt tct gta     446
Gly Leu Ile Ser Glu Leu Gln Asn Gln Asn Trp Arg Val Leu Ser Val
110                 115                 120                 125 gct aat gaa tgt agc ata gag gtt cct ggt gtt tta aat gtt caa agg     494
Ala Asn Glu Cys Ser Ile Glu Val Pro Gly Val Leu Asn Val Gln Arg
                130                 135                 140 ctt cag cag ttg ctt ctc acc ttg gct act cta ata aaa agg gaa cta     542
Leu Gln Gln Leu Leu Leu Thr Leu Ala Thr Leu Ile Lys Arg Glu Leu
            145                 150                 155 tgt gac tca tct gtt ctg gtg att gga tat ata atg aaa aaa tcc cgt     590
Cys Asp Ser Ser Val Leu Val Ile Gly Tyr Ile Met Lys Lys Ser Arg
        160                 165                 170 gag gaa gac ttc gca agg aga gga gca ttt ccc ata tat cct agt aag     638
Glu Glu Asp Phe Ala Arg Arg Gly Ala Phe Pro Ile Tyr Pro Ser Lys
    175                 180                 185
```

```
                                                              -continued ggc agt ctt atc ttt gtt ccc ctc tct ttt gaa ctt cct tta agt ttg        686
Gly Ser Leu Ile Phe Val Pro Leu Ser Phe Glu Leu Pro Leu Ser Leu
190             195                 200                 205 caa ctg caa gaa gtt gat atg gcc ctc cac aaa ata acc gat gag att        734
Gln Leu Gln Glu Val Asp Met Ala Leu His Lys Ile Thr Asp Glu Ile
                210                 215                 220 gtc aag att gat cca aac tgc tcc att gat ttt cca aaa ggg att tca        782
Val Lys Ile Asp Pro Asn Cys Ser Ile Asp Phe Pro Lys Gly Ile Ser
            225                 230                 235 ttt tct aca gga atg tct gaa att ata agg ttt gtg gaa gag cac cct        830
Phe Ser Thr Gly Met Ser Glu Ile Ile Arg Phe Val Glu Glu His Pro
        240                 245                 250 gat ttc cgc atc atg gat cca ttt aaa aac att tac cca ttg ctt gat        878
Asp Phe Arg Ile Met Asp Pro Phe Lys Asn Ile Tyr Pro Leu Leu Asp
    255                 260                 265 cgt ctt caa atc caa aaa atc ctt gtc cgg ttg caa gaa ctt ggc att        926
Arg Leu Gln Ile Gln Lys Ile Leu Val Arg Leu Gln Glu Leu Gly Ile
270                 275                 280                 285 gaa gga aag cca aaa ctt cga gca ccg tat tct tgc aag gtt gac aat        974
Glu Gly Lys Pro Lys Leu Arg Ala Pro Tyr Ser Cys Lys Val Asp Asn
                290                 295                 300 ttt gat aat ggt gaa ttg gat aag cat cta gca gaa gct aat tta tcc       1022
Phe Asp Asn Gly Glu Leu Asp Lys His Leu Ala Glu Ala Asn Leu Ser
            305                 310                 315 ttc cca ctc att gtg aag cca caa gtt gct tgt gga gtc gct gat gcc       1070
Phe Pro Leu Ile Val Lys Pro Gln Val Ala Cys Gly Val Ala Asp Ala
        320                 325                 330 cac aat atg gca ctg gtt ttt cag att gaa gaa ttt agc aac ctc agt       1118
His Asn Met Ala Leu Val Phe Gln Ile Glu Glu Phe Ser Asn Leu Ser
    335                 340                 345 gtg ccc ctt cct gct gtg cta cag gaa tac gtg gat cac gga tcc aag       1166
Val Pro Leu Pro Ala Val Leu Gln Glu Tyr Val Asp His Gly Ser Lys
350                 355                 360                 365 att ttc aag ttc tat gtg atc gga gac aag gtt ttc tac gcc gtt aga       1214
Ile Phe Lys Phe Tyr Val Ile Gly Asp Lys Val Phe Tyr Ala Val Arg
                370                 375                 380 gac tca atg ccc aac gcg cgc ttc ctt aag ccg tcg tca gga ggt gaa       1262
Asp Ser Met Pro Asn Ala Arg Phe Leu Lys Pro Ser Ser Gly Gly Glu
            385                 390                 395 gct ctt aca ttt aat agt ttg aag act ctt ccg gtg gct acc aat gag       1310
Ala Leu Thr Phe Asn Ser Leu Lys Thr Leu Pro Val Ala Thr Asn Glu
        400                 405                 410 cag cga ccg cag acc gcc gcg gaa gat ggc aag ctg tta gat gcc gat       1358
Gln Arg Pro Gln Thr Ala Ala Glu Asp Gly Lys Leu Leu Asp Ala Asp
    415                 420                 425 ctg gta gaa gag gcc gca aaa ttc ctg aag ggg ctg ctt ggg ctt aca       1406
Leu Val Glu Glu Ala Ala Lys Phe Leu Lys Gly Leu Leu Gly Leu Thr
430                 435                 440                 445 gta ttt gga ttc gat gtc gtc gtc caa gaa ggc acc gga gac cat gtc       1454
Val Phe Gly Phe Asp Val Val Val Gln Glu Gly Thr Gly Asp His Val
                450                 455                 460 ata gtg gac ctg aac tac ctg ccg tcg ttc aaa gag gtt ccc aac tcg       1502
Ile Val Asp Leu Asn Tyr Leu Pro Ser Phe Lys Glu Val Pro Asn Ser
            465                 470                 475 gag gcg gtg cct gca ttc tgg gac gcg gtc agg cag gcg tgc gag tcg       1550
Glu Ala Val Pro Ala Phe Trp Asp Ala Val Arg Gln Ala Cys Glu Ser
        480                 485                 490 acg cgc ggg aat gcg aat gtc cag ggt taa cctcaatgat cttcccgaat        1600
Thr Arg Gly Asn Ala Asn Val Gln Gly *
```

-continued

```
              495                 500
aataagtgaa tctacctgga gcgtagcaga gaggagagcc gcagtggtgt tcactggttg    1660
taatggtcag ctgtagctgt gggaataagt gaaatacaat ccgccaagtt tagctgtcga    1720
tctcgtcgcc gtggtgtatt ctgtcacgat gtcagtttca tgtgaatctg ctaactgatg    1780
gtttcccaaa aaaaaaaaaa aaaaaaaa                                       1808
```

<210> SEQ ID NO 14
<211> LENGTH: 502
<212> TYPE: PRT
<213> ORGANISM: Zea mays

<400> SEQUENCE: 14

```
Met Ala Thr Gly Arg Pro Val Arg Leu Val Leu Asp Ala Ser Leu Leu
 1               5                  10                  15

Leu Asp Pro Ser Ser Thr Arg Glu Ala Ala Val Ala Leu Arg Pro
                20                  25                  30

Gly Val Glu Glu Leu Leu Arg Arg Leu Arg Tyr Ser Asn Leu Asn Val
                35                  40                  45

Ala Ile Cys Tyr Ala Glu Gly Met Pro Asn Asn Glu Ser Gly Phe Leu
        50                  55                  60

Glu Lys Val Ala Ser Ser His Leu Phe Gly Ser Ile Ala Leu Leu Ala
65                  70                  75                  80

Lys Ser Gly Asn Leu Ser Leu Thr Glu Leu Met Leu Glu Trp Ser Arg
                85                  90                  95

Thr Ser Phe Cys Phe Tyr Ala Thr Ser Arg Val Asp Lys Gly Leu Ile
                100                 105                 110

Ser Glu Leu Gln Asn Gln Asn Trp Arg Val Leu Ser Val Ala Asn Glu
                115                 120                 125

Cys Ser Ile Glu Val Pro Gly Val Leu Asn Val Gln Arg Leu Gln Gln
        130                 135                 140

Leu Leu Leu Thr Leu Ala Thr Leu Ile Lys Arg Glu Leu Cys Asp Ser
145                 150                 155                 160

Ser Val Leu Val Ile Gly Tyr Ile Met Lys Lys Ser Arg Glu Glu Asp
                165                 170                 175

Phe Ala Arg Arg Gly Ala Phe Pro Ile Tyr Pro Ser Lys Gly Ser Leu
                180                 185                 190

Ile Phe Val Pro Leu Ser Phe Glu Leu Pro Leu Ser Leu Gln Leu Gln
        195                 200                 205

Glu Val Asp Met Ala Leu His Lys Ile Thr Asp Glu Ile Val Lys Ile
    210                 215                 220

Asp Pro Asn Cys Ser Ile Asp Phe Pro Lys Gly Ile Ser Phe Ser Thr
225                 230                 235                 240

Gly Met Ser Glu Ile Ile Arg Phe Val Glu Glu His Pro Asp Phe Arg
                245                 250                 255

Ile Met Asp Pro Phe Lys Asn Ile Tyr Pro Leu Leu Asp Arg Leu Gln
                260                 265                 270

Ile Gln Lys Ile Leu Val Arg Leu Gln Glu Leu Gly Ile Glu Gly Lys
        275                 280                 285

Pro Lys Leu Arg Ala Pro Tyr Ser Cys Lys Val Asp Asn Phe Asp Asn
    290                 295                 300

Gly Glu Leu Asp Lys His Leu Ala Glu Ala Asn Leu Ser Phe Pro Leu
305                 310                 315                 320

Ile Val Lys Pro Gln Val Ala Cys Gly Val Ala Asp Ala His Asn Met
```

```
                  325                 330                 335
Ala Leu Val Phe Gln Ile Glu Glu Phe Ser Asn Leu Ser Val Pro Leu
            340                 345                 350

Pro Ala Val Leu Gln Glu Tyr Val Asp His Gly Ser Lys Ile Phe Lys
            355                 360                 365

Phe Tyr Val Ile Gly Asp Lys Val Phe Tyr Ala Val Arg Asp Ser Met
        370                 375                 380

Pro Asn Ala Arg Phe Leu Lys Pro Ser Ser Gly Glu Ala Leu Thr
385                 390                 395                 400

Phe Asn Ser Leu Lys Thr Leu Pro Val Ala Thr Asn Glu Gln Arg Pro
                405                 410                 415

Gln Thr Ala Ala Glu Asp Gly Lys Leu Leu Asp Ala Asp Leu Val Glu
            420                 425                 430

Glu Ala Ala Lys Phe Leu Lys Gly Leu Leu Gly Leu Thr Val Phe Gly
            435                 440                 445

Phe Asp Val Val Val Gln Glu Gly Thr Gly Asp His Val Ile Val Asp
        450                 455                 460

Leu Asn Tyr Leu Pro Ser Phe Lys Glu Val Pro Asn Ser Glu Ala Val
465                 470                 475                 480

Pro Ala Phe Trp Asp Ala Val Arg Gln Ala Cys Glu Ser Thr Arg Gly
                485                 490                 495

Asn Ala Asn Val Gln Gly
            500

<210> SEQ ID NO 15
<211> LENGTH: 26
<212> TYPE: DNA
<213> ORGANISM: Artificial Sequence
<220> FEATURE:
<223> OTHER INFORMATION: forward primer for itpk

<400> SEQUENCE: 15
attcctcccg aacccgaccc gatggc                                        26

<210> SEQ ID NO 16
<211> LENGTH: 25
<212> TYPE: DNA
<213> ORGANISM: Artificial Sequence
<220> FEATURE:
<223> OTHER INFORMATION: reverse primer for itpk

<400> SEQUENCE: 16
cggaattcta atgaaaaacg agctc                                         25

<210> SEQ ID NO 17
<211> LENGTH: 22
<212> TYPE: DNA
<213> ORGANISM: Artificial Sequence
<220> FEATURE:
<223> OTHER INFORMATION: reverse primer for itpk

<400> SEQUENCE: 17
caaccatgtt gtcgtgaaat aa                                            22

<210> SEQ ID NO 18
<211> LENGTH: 48
<212> TYPE: DNA
<213> ORGANISM: Artificial Sequence
<220> FEATURE:
<223> OTHER INFORMATION: PCR primer to create SmaI site for itpk-2
```

```
<400> SEQUENCE: 18
tatcacccgg atggtgtcg ggcgtgtgcg tggggacgga ggggcagg              48

<210> SEQ ID NO 19
<211> LENGTH: 38
<212> TYPE: DNA
<213> ORGANISM: Artificial Sequence
<220> FEATURE:
<223> OTHER INFORMATION: PCR primer to create NotI site for itpk2

<400> SEQUENCE: 19
atctagtaac ggtgcggccg cccgagtagt ctcctcgc                        38

<210> SEQ ID NO 20
<211> LENGTH: 41
<212> TYPE: DNA
<213> ORGANISM: Artificial Sequence
<220> FEATURE:
<223> OTHER INFORMATION: PCR primer to create SmaI site for itpk3

<400> SEQUENCE: 20
actcgtaaca tgaagccacc cgggatgcgc ggtgcacgcg g                    41

<210> SEQ ID NO 21
<211> LENGTH: 40
<212> TYPE: DNA
<213> ORGANISM: Artificial Sequence
<220> FEATURE:
<223> OTHER INFORMATION: PCR primer to create NotI site for itpk3

<400> SEQUENCE: 21
ctagtaacgg tgcggccgct taagtacctt ttgtacttgc                      40

<210> SEQ ID NO 22
<211> LENGTH: 26
<212> TYPE: DNA
<213> ORGANISM: Artificial Sequence
<220> FEATURE:
<223> OTHER INFORMATION: reverse primer for itpk5

<400> SEQUENCE: 22
catcttattt cacgacaaca tggttg                                     26

<210> SEQ ID NO 23
<211> LENGTH: 27
<212> TYPE: DNA
<213> ORGANISM: Artificial Sequence
<220> FEATURE:
<223> OTHER INFORMATION: TUSC primer for itpk5

<400> SEQUENCE: 23
ccgaagaagc agcaaagctt catccag                                    27

<210> SEQ ID NO 24
<211> LENGTH: 27
<212> TYPE: DNA
<213> ORGANISM: Artificial Sequence
<220> FEATURE:
<223> OTHER INFORMATION: TUSC primer for itpk5

<400> SEQUENCE: 24
tggtttggaa agagctagga ggtcctc                                    27

<210> SEQ ID NO 25
<211> LENGTH: 32
```

```
<212> TYPE: DNA
<213> ORGANISM: Artificial Sequence
<220> FEATURE:
<223> OTHER INFORMATION: TUSC Mu primer
<220> FEATURE:
<221> NAME/KEY: misc_feature
<222> LOCATION: (1)...(32)
<223> OTHER INFORMATION: w = A, or T
<220> FEATURE:
<221> NAME/KEY: misc_feature
<222> LOCATION: (1)...(32)
<223> OTHER INFORMATION: y = C, or T

<400> SEQUENCE: 25
agagaagcca acgccawcgc ctcyatttcg tc                                 32

<210> SEQ ID NO 26
<211> LENGTH: 36
<212> TYPE: DNA
<213> ORGANISM: Artificial Sequence
<220> FEATURE:
<223> OTHER INFORMATION: Sal A-20 poly A primer

<400> SEQUENCE: 26
tcgacccacg cgtccgaaaa aaaaaaaaaa aaaaaa                             36

<210> SEQ ID NO 27
<211> LENGTH: 24
<212> TYPE: DNA
<213> ORGANISM: Artificial Sequence
<220> FEATURE:
<223> OTHER INFORMATION: reverse primer for ITPK

<400> SEQUENCE: 27
agctcgtttt tcattagaat tccg                                          24

<210> SEQ ID NO 28
<211> LENGTH: 1364
<212> TYPE: DNA
<213> ORGANISM: Zea mays
<220> FEATURE:
<221> NAME/KEY: CDS
<222> LOCATION: (34)...(138)

<400> SEQUENCE: 28
gaattcgccc ttattcctcc cgaacccgac ccg atg gcc tcc gac gcc gcc gcc   54
                                    Met Ala Ser Asp Ala Ala Ala
                                      1               5 gag ccc tcc tcc ggc gtc acc cac ccc ccg cgc tac gtc atc ggt tac  102
Glu Pro Ser Ser Gly Val Thr His Pro Pro Arg Tyr Val Ile Gly Tyr
        10                  15                  20 gcg ctc gcg ccg aag aag cag cag agc ttc atc tag ccgtcgctgg        148
Ala Leu Ala Pro Lys Lys Gln Gln Ser Phe Ile *
            25                  30 tggcccaggc ggcgtcgcgg ggcatggacc tcgtccccgt ggatgcgtcg cagcccctcg  208
cagagcaagg gcccttccac ctcctcatcc acaagctcta cggagacgac tggcgcgccc  268
agctcgtggc cttcgccgcg cgccaccccg gccgtccccat cgtcgacccg ccccacgcca  328
tcgaccgcct ccacaaccgc atctccatgc tccaggtcgt ctccgagctc gaccacgccg  388
ccgaccagga cagcactttc ggtatcccca gccaggtcgt cgtctacgac gccgccgcgc  448
tgccgacttc ggactccctt gccgcgctcc gcttcccgct catcgccaag cccctcgtcg  508
ccgacggcac cgccaagtcc cacaagatgt cgctcgtcta ccaccgcgag ggcctcggca  568
agctccgccc gccgcttgtg ctccaggagt tcgtcaacca tggcggcgtc atcttcaagg  628
```

```
tctacgtcgt cggcggccac gtcacttgcg tcaagcgccg tagccttccc gacgtgtccc      688
ccgaggatga cgcatcggcc cagggatccg tctccttctc ccaggtctcc aacctcccca      748
ctgagcgcac ggcggaggag tactacggcg aaaagagtct cgaggacgcc gtcgtgccgc      808
ccgccgcatt catcaaccag atcgcgggcg gcctccgccg cgcgctgggc ctgcaactct      868
tcaacttcga catgatccgc gacgtccgcg ccggcgaccg ctatctcgtc attgacatca      928
actacttccc gggctacgcc aagatgccag gatacgagac tgtcctcacg gatttcttct      988
gggagatggt ccatgaggac ggcgtgggca accaacagga ggagaaaggg gccaaccatg     1048
ttgtcgtgaa ataagatgat gattgatggc actggatatc tggcgaatgc tgctgattct     1108
ggatgcagaa ttcgatgagg ggatttagtt ggttgtagta tctggcgaat gctgctggtt     1168
ctggatgcag aatttgatga ggggatttag ttggatttca acccacagca tgccgaggac     1228
ctcctagctc tttccagacc agttgtttag gtatcttttc tgggtaagtc agcttcatct     1288
agtttagtct gtctgaacaa aagagtggga catgacccra acggaattct atgaaaaacg     1348
agctaagggc gaattc                                                      1364

<210> SEQ ID NO 29
<211> LENGTH: 34
<212> TYPE: PRT
<213> ORGANISM: Zea mays

<400> SEQUENCE: 29

Met Ala Ser Asp Ala Ala Ala Glu Pro Ser Ser Gly Val Thr His Pro
1               5                   10                  15

Pro Arg Tyr Val Ile Gly Tyr Ala Leu Ala Pro Lys Lys Gln Gln Ser
            20                  25                  30

Phe Ile
```

PHYTATE POLYNUCLEOTIDES AND METHODS OF USE

CROSS-REFERENCE TO RELATED APPLICATIONS

This application is a divisional application of U.S. application Ser. No. 10/255,817 filed Sep. 26, 2002, now abandoned, and claims the benefit of U.S. Application Ser. No. 60/325,308 filed Sep. 27, 2001, all of which are herein incorporated by reference.

TECHNICAL FIELD

The present invention relates to the field of animal nutrition. Specifically, the present invention relates to the identification and use of genes encoding enzymes involved in the metabolism of phytate in plants and the use of these genes and mutants thereof to reduce the levels of phytate, and/or increase the levels of non-phytate phosphorus in food or feed.

BACKGROUND OF THE INVENTION

The role of phosphorous in animal nutrition is well recognized, it is a critical component of the skeleton, nucleic acids, cell membranes and some vitamins. Though phosphorous is essential for the health of animals, not all phosphorous in feed is bioavailable.

Phytates are the major form of phosphorous in seeds, for example phytate represents about 60-80% of total phosphorous in corn and soybean. When seed-based diets are fed to non-ruminants, the consumed phytic acid forms salts with several important mineral nutrients, such as potassium, calcium, and iron, and also binds proteins in the intestinal tract. These phytate complexes cannot be metabolized by monogastric animals and are excreted, effectively acting as antinutritional factors by reducing the bioavailability of dietary phosphorous and minerals. Phytate-bound phosphorous in animal excreta also has a negative environmental impact, contributing to surface and ground water pollution.

There have been two major approaches to reducing the negative nutritional and environmental impacts of phytate in seed. The first involves post-harvest interventions, which increase the cost and processing time of feed. Post-harvest processing technologies remove phytic acid by fermentation or by the addition of compounds, such as phytases.

The second is a genetic approach. One genetic approach involves developing crop germplasm with heritable reductions in seed phytic acid. While some variability for phytic acid was observed, there was no change in non-phytate phosphorous. Further, only 2% of the observed variation in phytic acid was heritable, whereas 98% of the variation was attributed to environmental factors.

Another genetic approach involves selecting low phytate lines from a mutagenized population to produce germplasm. Most mutant lines are a loss of function, presumably blocked in the phytic acid biosynthetic pathway, therefore low phytic acid accumulation will likely be a recessive trait. In certain cases, this approach has revealed that homozygosity for substantially reduced phytate proved lethal.

Another genetic approach is transgenic technology, which has been used to increase phytase levels in plants. These transgenic plant tissues or seed have been used as dietary supplements.

The biosynthetic route leading to phytate is complex and not completely understood. Without wishing to be bound by any particular theory of the formation of phytate, it is believed that the synthesis may be mediated by a series of one or more ADP-phosphotransferases, ATP-dependent kinases and isomerases. A number of intermediates have been isolated including, for example, monophosphates such as D-myo-inositol 3-monophosphate, diphosphates ($IP_2$s) such as D-myo-inositol 3,4-bisphosphate, trisphosphates ($IP_3$s) such as D-myo-inositol 3,4,6 trisphosphate, tetraphosphates ($IP_4$s) such as D-myo-inositol 3,4,5,6-tetrakisphosphates, and pentaphosphates ($IP_5$s) such as D-myo-inositol 1,3,4,5,6 pentakisphosphate. The phosphorylation of the $IP_5$ to $IP_6$ is found to be reversible. Several futile cycles of dephosphorylation and rephosphorylation of the $IP_5$ and $IP_6$ forms have been reported as well as a cycle involving glucose-6-phosphate->D-myo-inositol 3-monophosphate->myo-inositol; the last step being completely reversible, indicating that control of metabolic flux through this pathway may be important.

Based on the foregoing, there exists the need to improve the nutritional content of plants, particularly corn and soybean by increasing non-phytate phosphorous and reducing seed phytate. This invention provides tools and reagents that allow the skilled artisan, by the application of, inter alia, transgenic methodologies to influence the metabolic flux in respect to the phytic acid pathway.

SUMMARY OF THE INVENTION

Inositol 1,3,4-trisphosphate 5/6-kinases (ITPK) are involved in the phytate biosynthetic pathway. This invention provides nucleic acids and proteins related to inositol 1,3,4-trisphosphate 5/6-kinases as well as recombinant expression cassettes and methods to modulate the level of inositol 1,3,4-trisphosphate 5/6kinases in host cells, transgenic plants and seeds. The invention also provides the host cells, transgenic plants and transgenic seeds produced by these methods. The invention foresees using these nucleic acids or polypeptides, or variants thereof, to modulate the flux through the phytic acid biosynthetic pathway in order to improve the nutritional quality of feed, corn and soy in particular, and to reduce the environmental impact of animal waste by creating seed with higher available phosphorous or lower phytate levels.

DETAILED DESCRIPTION OF THE INVENTION

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, the term "nucleic acid" means a polynucleotide and includes single or multi-stranded polymers of deoxyribonucleotide or ribonucleotide bases. Nucleic acids may also include fragments and modified nucleotides. Therefore, as used herein, the terms "nucleic acid" and "polynucleotide" are used interchangably.

As used herein, "inositol 1,3,4-trisphosphate 5/6-kinase polynucleotide" or "ITPK polynucleotide" means a polynucleotide encoding a polypeptide with inositol 1,3,4-trisphosphate 5/6-kinase activity, or a polynucleotide capable of modulating the expression of mRNA or protein in a host cell. The term is also inclusive of fragments, variants, homologues, alleles or precursors with the any one of the above stated functions.

As used herein, "ITPK" means inositol 1,3,4-trisphosphate 5/6-kinase in regards to any nucleic acid or polypeptide, or the associated functional activity.

As used herein, "polypeptide" means proteins, protein fragments, modified proteins (e.g., glycosylated, phosphorylated, or other modifications), amino acid sequences and synthetic amino acid sequences. The polypeptide can be modified or not. Therefore, as used herein, "polypeptide" and "protein" are used interchangably.

As used herein, "inositol 1,3,4-trisphosphate 5/6-kinase polypeptide" or "ITPK polypeptide" which is capable of phosphorylating an appropriate inositol phosphate substrate and refers to one or more amino acid sequences, in modified or unmodified form. The term is also inclusive of active fragments, variants, homologs, alleles or precursors (e.g., preproproteins or proproteins) or activity thereof.

As used herein, "plant" includes plants and plant parts including but not limited to plant cells and plant tissues such as leaves, stems, roots, flowers, pollen, and seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid, functional fragments. Alternatively, fragments of a nucleotide sequence that can be useful as hybridization probes may not encode fragment proteins retaining biological activity. Thus, fragments of a nucleotide sequence are generally greater than 25, 50, 100, 150, 200, 250, 300, 350, 400, 450, 500, 600, or 700 nucleotides and up to and including the entire nucleotide sequence encoding the proteins of the invention. Generally the probes are less than 1000 nucleotides and often less than 500 nucleotides. Fragments of the invention include antisense sequences used to decrease expression of the inventive polynucleotides. Such antisense fragments may vary in length ranging from greater than 25, 50, 100, 200, 300, 400, 500, 600, or 700 nucleotides and up to and including the entire coding sequence.

By "functional equivalent" as applied to a polynucleotide or a protein is intended a polynucleotide or a protein of sufficient length to modulate the level of ITPK protein activity in a plant cell. A polynucleotide functional equivalent can be in sense or antisense orientation.

By "variants" is intended substantially similar sequences. Generally, nucleic acid sequence variants of the invention will have at least 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98% or 99% sequence identity to the native nucleotide sequence, wherein the % sequence identity is based on the entire sequence and is determined by GAP 10 analysis using default parameters. Generally, polypeptide sequence variants of the invention will have at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the native protein, wherein the % sequence identity is based on the entire sequence and is determined by GAP 10 analysis using default parameters. GAP uses the algorithm of Needleman and Wunsch (*J. Mol. Biol.* 48:443-453, 1970) to find the alignment of two complete sequences that maximizes the number of matches and minimizes the number of gaps.

As used herein "transformation" may include stable transformation and transient transformation. Unless otherwise stated, "transformation" refers to stable transformation.

As used herein "stable transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimeraplasty or transposon insertion.

As used herein "transient transformation" refers to the transfer of a nucleic acid fragment or protein into the nucleus (or DNA-containing organelle) of a host organism resulting in gene expression without integration and stable inheritance.

"ITPK enzyme-binding molecule", as used herein, refers to molecules or ions which bind or interact specifically with phytate biosynthetic enzyme polypeptides or polynucleotides of the present invention, including, for example enzyme substrates, cofactors, antagonists, inhibitors, cell membrane components and classical receptors. Binding between polypeptides of the invention and such molecules, including binding or interaction molecules may be exclusive to polypeptides of the invention, or it may be highly specific for polypeptides of the invention, or it may be highly specific to a group of proteins that includes polypeptides of the invention, or it may be specific to several groups of proteins at least one of which includes a polypeptide of the invention. Binding molecules also include antibodies and antibody-derived reagents that bind specifically to polypeptides of the invention.

"High phosphorous transgenic", as used herein, means an entity which, as a result of recombinant genetic manipulation, produces seed with a heritable decrease in phytic acid percentage and/or increase in non-phytate phosphorous percentage as compared to a corresponding plant that has not been transformed.

"Phytic acid", as used herein, means myo-inositol tetraphosphoric acid, myo-inositol pentaphosphoric acid or myo-inositol hexaphosphoric acid. As a salt with cations, phytic acid is "phytate".

"Non-phytate phosphorous", as used herein, means total phosphorus minus phytate phosphorous.

"Non-ruminant animal" means an animal with a simple stomach divided into the esophageal, cardia, fundus and pylorus regions. A non-ruminant animal additionally implies a species of animal without a functional rumen. A rumen is a section of the digestive system where feedstuff/food is soaked and subjected to digestion by microorganisms before passing on through the digestive tract. This phenomenon does not occur in a non-ruminant animal. The term non-ruminant animal includes but is not limited to humans, swine, poultry, cats and dogs.

Nucleic Acids

Inositol 1,3,4-trisphosphate 5/6 kinases (ITPKs) are involved in the phytate biosynthetic pathway. The enzymes of the present invention have a broader substrate specificity than expected and can phosphorylate several $IP_3$ and $IP_4$ inositol phosphate species using adenosine triphosphate (ATP) as the phosphate donor, resulting in the products adenosine diphosphate (ADP) and a phosphorylated inositol phosphate. It is expected that this enzyme acts sufficiently downstream of myo-inositol in the phytate pathway so that modulation of this enzyme may decrease phytate accumulation without significantly impacting myo-inositol levels. The sequences of the present invention have homology throughout the entire sequence to known ITPK nucleic acids and proteins. It is expected that modulating the expression and/or level of the nucleic acids of the present invention will modulate the phytate biosynthetic pathway providing methods to increase available phosphorous, decrease phytate and/or decrease polluting phytate-bound phosphorous in animal waste.

The isolated nucleic acids of the present invention can be made using (a) standard recombinant methods, (b) synthetic techniques, or combinations thereof. In some embodiments, the polynucleotides of the present invention can be cloned, amplified, or otherwise constructed from a monocot or dicot. Typical examples of monocots are corn, sorghum, barley, wheat, millet, rice, or turf grass. Typical dicots include soybeans, safflower, sunflower, canola, alfalfa, potato, or cassaya.

Functional fragments included in the invention can be obtained using primers which selectively hybridize under stringent conditions. Primers are generally at least 12 bases in length and can be as high as 200 bases, but will generally be from 15 to 75, or more likely from 15 to 50 bases. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, pages 8.0.3-8.5.9 *Current Protocols in Molecular Biology*, Ausubel et al., Eds., Greene Publishing and Wiley-Interscience, New York (1995). Also, see generally, McPherson (ed.), *DIRECTED MUTAGENESIS: A Practical Approach*, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alter, add or delete a single amino acid or a small percentage of amino acids in the encoded sequence. A "conservatively modified variant" is an alteration which results in the substitution of an amino acid with a chemically similar amino acid. When the nucleic acid is prepared or altered synthetically, advantage can be taken of known codon preferences of the intended host.

With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the claimed invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

For example, the following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company, other acceptable conservative substitution patterns known in the art may also be used, such as the scoring matrices of sequence comparison programs like the GCG package, BLAST, or CLUSTAL for example.

The claimed invention also includes "shufflents" produced by sequence shuffling of the inventive polynucleotides to obtain a desired characteristic. Sequence shuffling is described in PCT publication No. 96/19256. See also, Zhang, J. H., et al., *Proc. Natl. Acad. Sci. USA* 94:4504-4509 (1997).

The present invention also includes the use of 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)).

Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. Cell. Biol.* 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387-395 (1984)) or MacVector 4.1 (Eastman Kodak Co., New Haven, Conn.).

For example, the inventive nucleic acids can be optimized for enhanced expression in plants of interest. See, for example, Perlak et al. (1991) *Proc. Natl. Acad. Sci. USA* 88:3324-3328; and Murray et al. (1989) *Nucleic Acids Res.* 17:477-498, the disclosure of which is incorporated herein by reference. In this manner, the polynucleotides can be synthesized utilizing plant-preferred codons.

The present invention provides subsequences comprising isolated nucleic acids containing at least 20 contiguous bases of the claimed sequences. For example the isolated nucleic acid includes those comprising at least 20, 30, 40, 50, 60, 70, 80, 90, 100, 200, 300, 400, 500, 600, 700 or 800 contiguous nucleotides of the claimed sequences. Subsequences of the isolated nucleic acid can be used to modulate or detect gene expression by introducing into the subsequences compounds which bind, intercalate, cleave and/or crosslink to nucleic acids.

The nucleic acids of the claimed invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence, or a GST fusion sequence, provides a convenient means to purify the proteins of the claimed invention.

A polynucleotide of the claimed invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics* 37:327-336 (1996). Other methods for producing full-length libraries are known in the art. See, e.g., Edery et al., *Mol. Cell Biol.* 15(6):3363-3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705-5711 (1990); Patanjali et al., *Proc. Natl. Acad. U.S.A.* 88:1943-1947 (1991); U.S. Pat. Nos. 5,482,685 and 5,637,685; and Soares et al., *Proc. Natl. Acad. Sci. USA* 91:9228-9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique* 3(2):58-63 (1991); Sive and St. John, *Nucl. Acids Res.* 16(22):10937 (1988); *Current Protocols in Molecular Biology*, Ausubel et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1-3 (1989), *Methods in Enzymology*, Vol. 152: Guide to Molecular Cloning Techniques, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related polynucleotides directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. *BioTechniques*, 22(3):481-486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues such as ears, seedlings, leaves, stalks, roots, pollen, or seeds. Good results have been obtained using tissues such as night-harvested earshoot with husk at stage V-12 from corn line B73, corn night-harvested leaf tissue at stage V8-V10 from line B73, corn anther tissue at prophase I from line B73, 4 DAP coenocytic embryo sacs from corn line B73, 67 day old corn cob from corn line L, and corn BMS suspension cells treated with chemicals related to phosphatases.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2nd ed., Cold Spring Harbor Laboratory Press, Plainview, N.Y.) and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90-99 (1979); the phosphodiester method of Brown et al., *Meth. Enzymol.* 68:109-151 (1979); the diethylphosphoramidite method of Beaucage et al., *Tetra. Lett.* 22:1859-1862 (1981); the solid phase phosphoramidite triester method described by Beaucage and Caruthers, *Tetra. Lett.* 22(20): 1859-1862 (1981), e.g., using an automated synthesizer, e.g., as described in Needham-VanDevanter et al., *Nucleic Acids Res.* 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The nucleic acids of the claimed invention include those amplified using the following primer pairs: SEQ ID NO: 15 paired with SEQ ID NO: 16, 17, 22 or 27.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual*; Cold Spring Harbor, N.Y.; (1989); Gelvin et al.; *Plant Molecular Biology Manual* (1990); Plant Biotechnology: Commercial Prospects and Problems, eds. Prakash et al.; Oxford & IBH Publishing Co.; New Delhi, India; (1993); and Heslot et al.; *Molecular Biology and Genetic Engineering of Yeasts*; CRC Press, Inc., USA; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the actin promoter, the ubiquitin promoter, the histone H2B promoter (Nakayama et al., 1992, FEBS Lett 30:167-170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the pepcarboxylase promoter which is light induced.

Examples of promoters under developmental control include promoters that initiate transcription preferentially in certain tissues, such as leaves, roots, fruit, pollen, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, (Boronat, A., et al., Plant Sci. 47:95-102 (1986); Reina, M., et al., Nucleic Acids Res. 18(21):6426 (1990); Kloesgen, R. B., et al., Mol. Gen. Genet. 203:237-244 (1986)), as well as the globulin 1, oleosin and the phaseolin promoters. The disclosures each of these are incorporated herein by reference in their entirety.

The barley or maize Nuc1 promoter, the maize Cim1 promoter or the maize LTP2 promoter can be used to preferentially express in the nucellus. See, for example WO 00/11177, the disclosure of which is incorporated herein by reference.

Either heterologous or non-heterologous (i.e., endogenous) promoters can be employed to direct expression of the nucleic acids of the present invention. These promoters can also be used, for example, in expression cassettes to drive expression of sense nucleic acids or antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, Mol. Cell Biol. 8:4395-4405 (1988); Callis et al., Genes Dev. 1:1183-1200 (1987). Use of maize introns Adh1-S intron 1, 2, and 6, the Bronze-1 intron are known in the art. See generally, The Maize Handbook, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene encodes antibiotic or herbicide resistance. Suitable genes include those coding for resistance to the antibiotics spectinomycin and streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of Agrobacterium tumefaciens described by Rogers et al., Meth. In Enzymol. 153:253-277 (1987). Exemplary A. tumefaciens vectors useful herein are plasmids pKYLX6 and pKYLX7 of Schardl et al., Gene 61:1-11 (1987) and Berger et al., Proc. Natl. Acad. Sci. USA 86:8402-8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the claimed invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., Proc. Natl. Acad. Sci. USA 85:8805-8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., The Plant Cell 2:279-289 (1990) and U.S. Pat. No. 5,034,323. Recent work has shown suppression with the use of double stranded RNA. Such work is described in Tabara et al., Science 282:5388:430-431 (1998). Hairpin approaches of gene suppression are disclosed in WO 98/53083 and WO 99/53050.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., Nucleic Acids Res (1986) 14:4065-4076, describe covalent bonding of a single-stranded DNA fragment with alkylating derivatives of nucleotides complementary to target sequences. A report of similar work by the same group is that by Knorre, D. G., et al., Biochimie (1985) 67:785-789. Iverson and Dervan also showed sequence-specific cleavage of single-stranded DNA mediated by incorporation of a modified nucleotide which was capable of activating cleavage (J. Am. Chem. Soc. (1987) 109:1241-1243). Meyer, R. B., et al., J. Am. Chem. Soc. (1989) 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197-3203. Use of crosslinking in triple-helix forming probes was also disclosed by Home et al., J. Am. Chem. Soc. (1990) 112:2435-2437. Use of N4, N4-ethanocytosine as an alkylating agent to crosslink to single-stranded oligonucleotides has also been described by Webb and Matteucci, *J. Am. Chem. Soc.* (1986) 108:2764-2765; Nucleic Acids Res (1986) 14:7661-7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681941.

Gene or Trait Stacking

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of ITPK-2, ITPK-3, ITPK-4, ITPK-5, ITPK-6, and ITPK-7 (SEQ ID NOS: 1, 3, 5, 7, 9, 11 and 13), or with other genes implicated in phytic acid metabolic pathways such as phytase; Lpa1, Lpa2 (see U.S. Pat. Nos. 5,689,054 and 6,111,168); myo-inositol 1-phosphate synthase (MI1PS), inositol polyphosphate kinase (IPPK), and myo-inositol monophosphatase (IMP) (see WO 99/05298 and U.S. application Ser. No. 10/042,465 filed Jan. 9, 2002) and the like, the disclosures of which are herein incorporated by reference. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combine with any combination of other suppression cassettes or overexpression cassettes to generate the desired combination of traits in the plant.

Proteins

ITPK proteins are involved in the phosphorylation of appropriate inositol phosphate substrates in inositol phosphate metabolism. These enzymes have a broader substrate specificity than earlier suspected and can phosphorylate various species of $IP_3$ and $IP_4$, using ATP as the phosphate donor. The proteins of the present invention show homology to known ITPK sequences, with the sequence similarity distributed across the entire sequence. It is expected that modulation of the expression of these proteins of the present invention will provide methods to improve the quality of animal feed by reducing the level of phytate and/or increasing the level of bioavailable phosphorous. Reducing phytate levels could also result in less environment-polluting phosphorous in the waste of non-ruminant animals.

Proteins of the present invention include proteins having the disclosed sequences as well proteins coded by the disclosed polynucleotides. In addition, proteins of the present invention include proteins derived from the native protein by deletion, addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants can generally be made such that variants continue to possess the desired activity.

The isolated proteins of the present invention include a polypeptide comprising at least 25 contiguous amino acids encoded by any one of the nucleic acids of the present invention, or polypeptides that are conservatively modified variants thereof. The proteins of the present invention or variants thereof can comprise any number of contiguous amino acid residues from a polypeptide of the present invention, wherein that number is selected from the group of integers consisting of from 25 to the number of residues in a full-length polypeptide of the present invention. Optionally, this subsequence of contiguous amino acids is at least 25, 30, 40, 50, 60, 70, 80, 90, 100, 150, 200, 250, 300, 350, 400, 450, or 500 amino acids in length.

The present invention includes catalytically active polypeptides (i.e., enzymes). Catalytically active polypeptides will generally have a specific activity of at least about 20%, 30%, 40%, 50%, 60%, 70%, 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least about 30%, 40%, 50%, 60%, 70%, 80%, 90%, or 95% that of the native (non-synthetic), endogenous polypeptide. Methods of assaying and quantifying measures of enzymatic activity and substrate specificity ($k_{cat}/K_m$), are well known to those of skill in the art. See, e.g., Segel, *Biochemical Calculations*, $2^{nd}$ ed., John Wiley and Sons, New York (1976).

The present invention includes modifications that can be made to an inventive protein. In particular, it may be desirable to diminish the activity of the gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in recombinantly engineered cells such as bacteria, yeast, insect, mammalian, or plant cells. The cells produce the protein in a non-natural condition (e.g., in quantity, composition, location, and/or time), because they have been genetically altered through human intervention to do so.

Typically, an intermediate host cell may be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes and eukaryotes. Prokaryotes include bacterial hosts such as *Eschericia coli*, *Salmonella typhimurium*, and *Serratia marcescens*. Eukaryotic hosts such as yeast, insect cells or filamentous fungi may also be used in this invention.

Commonly used prokaryotic control sequences include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva et al., *Gene* 22:229-235 (1983); Mosbach et al., *Nature* 302:543-545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The baculovirus expression system (BES) is a eukaryotic, helper-independent expression system which has been used to express hundreds of foreign genes (Luckow, V., Ch. 4 "Cloning and Expression of Heterologous Genes in Insect Cells with Baculovirus Vectors" in *Recombinant DNA Technology and Applications*, A. Prokop et al., Eds. McGraw-Hill, Inc. (1991); Luckow, V., Ch. 10 "Insect Expression Technology" in *Principles & Practice of Protein Engineering*, J. L. Cleland and C. S. Craig, Eds. John Wiley & Sons, (1994)).

Recombinant baculoviruses are generated by inserting the particular gene- or genes-of-interest into the baculovirus genome using established protocols with vectors and reagents from commercial suppliers (e.g., Invitrogen, Life Technologies Incorporated). Commercial vectors are readily available with various promoters, such as polyhedrin and p10, optional signal sequences for protein secretion, or affinity tags, such as 6× histidine. These recombinant viruses are grown, maintained and propagated in commercially available cell lines derived from several insect species including *Spodoptera frugiperda* and *Trichoplusia ni*. The insect cells can be cultured using well-established protocols in a variety of different media, for example, with and without bovine serum supplementation. The cultured cells are infected with the recombinant viruses and the gene-of-interest polypeptide is expressed. Proteins expressed with the baculovirus system have been extensively characterized and, in many cases, their post-translational modifications such as phosphorylation, acylation, etc., are identical to the natively expressed protein.

A protein of the present invention, once expressed, can be isolated from cells by lysing the cells and applying standard protein isolation techniques to the lysates. The monitoring of the purification process can be accomplished by using Western blot techniques or radioimmunoassay or other standard immunoassay techniques. Expression cassettes are also available which direct the expressed protein to be secreted from the cell into the media. In these cases, the expressed protein can be purified from the cell growth media using standard protein purification techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A.*; Merrifield et al., *J. Am. Chem. Soc.* 85:2149-2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide)) are known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the claimed invention in a plant or part thereof. Modulation can be effected by increasing or decreasing the concentration and/or the composition (i.e., the ratio of the polypeptides of the claimed invention) in a plant.

The method comprises transforming a plant cell with an expression cassette comprising a polynucleotide of the present invention to obtain a transformed plant cell, growing the transformed plant cell under conditions allowing expression of the polynucleotide in the plant cell in an amount sufficient to modulate concentration and/or composition in the plant cell.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, content of the polypeptide is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In certain embodiments, the polypeptides of the present invention are modulated in monocots or dicots, for example maize, soybeans, sunflower, safflower, sorghum, canola, wheat, alfalfa, rice, barley and millet.

Means of detecting the proteins of the present invention are not critical aspects of the present invention. The proteins can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand molecule (e.g., streptavidin) which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of catalytically active polypeptides of the present invention. The method comprises contacting a polypeptide of the present invention with a compound whose ability to bind to or modulate enzyme activity is to be determined. The polypeptide employed will have at least 20%, 30%, 40%, 50%, 60%, 70%, 80%, 90% or 95% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, $2^{nd}$ ed., Academic Press, New York, N.Y. (1986); and Kohler and Milstein, *Nature* 256:495-497 (1975).

Other suitable techniques involve selection of libraries of recombinant antibodies in phage or similar vectors (see, e.g., Huse et al., *Science* 246:1275-1281 (1989); and Ward et al., *Nature* 341:544-546 (1989); and Vaughan et al., *Nature Biotechnology* 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.* 14:845-851 (1996). Also, recombinant immunoglobulins may be produced. See, Cabilly, U.S. Pat. No. 4,816,567; and Queen et al., *Proc. Natl. Acad. Sci. U.S.A.* 86:10029-10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention may be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transformation of Cells

The method of transformation is not critical to the present invention; various methods of transformation are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein, can be used to construct an expression cassette which can be introduced into the desired plant. Isolated nucleic acid acids of the present invention can be introduced into plants according to techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in *Plant Cell, Tissue and Organ Culture, Fundamental Methods*, Eds. O. L. Gamborg and G. C. Phillips, Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci. U.S.A.* 82:5824 (1985). Ballistic transformation techniques are described in Klein et al., *Nature* 327:70-73 (1987).

*Agrobacterium tumefaciens*-meditated transformation techniques are well described in the scientific literature. See, for example Horsch et al., *Science* 233:496-498 (1984), and Fraley et al., Proc. Natl. Acad. Sci. 80:4803 (1983). For instance, *Agrobacterium* transformation of maize is described in U.S. Pat. No. 5,981,840. *Agrobacterium* transformation of soybean is described in U.S. Pat. No. 5,563,055.

Other methods of transformation include (1) *Agrobacterium rhizogenes*-mediated transformation (see, e.g., Lichtenstein and Fuller In: *Genetic Engineering*, Vol. 6, P. W. J. Rigby, Ed., London, Academic Press, 1987; and Lichtenstein, C. P. and Draper, J. In: *DNA Cloning*, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., *Plant Cell Physiol.* 25:1353 (1984)), and (3) the vortexing method (see, e.g., Kindle, *Proc. Natl. Acad. Sci. USA* 87:1228 (1990)).

DNA can also be introduced into plants by direct DNA transfer into pollen as described by Zhou et al., *Methods in Enzymology* 101:433 (1983); D. Hess, *Intern Rev. Cytol.*, 107:367 (1987); Luo et al., *Plant Mol. Biol. Reporter* 6:165 (1988). Expression of polypeptide coding polynucleotides can be obtained by injection of the DNA into reproductive organs of a plant as described by Pena et al., *Nature* 325:274 (1987). DNA can also be injected directly into the cells of immature embryos and the rehydration of desiccated embryos as described by Neuhaus et al., *Theor. Appl. Genet* 75:30 (1987); and Benbrook et al., in *Proceedings Bio Expo* 1986, Butterworth, Stoneham, Mass., pp. 27-54 (1986).

Animal and lower eukaryotic (e.g., yeast) host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell* 2:603-618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* can be achieved as described by Horsch et al., *Science*, 227:1229-1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. Plant Phys.* 38:467-486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Transgenic plants of the present invention can be homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated. Alternatively, propagation of heterozygous transgenic plants could be accomplished through apomixis.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: *Genome Mapping in Plants* (ed. Andrew H. Paterson) by Academic Press/R. G. Landis Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants which can be used in the method of the invention include monocotyledonous and dicotyledonous plants. Preferred plants include maize, wheat, rice, barley, oats, sorghum, millet, rye, soybean, sunflower, safflower, alfalfa, canola, cotton, or turf grass.

Seeds derived from plants regenerated from transformed plant cells, plant parts or plant tissues, or progeny derived from the regenerated transformed plants, may be used directly as feed or food, or further processing may occur.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

Other objects, features, advantages and aspects of the present invention will become apparent to those of skill from the following description. It should be understood, however, that the following description and the specific examples, while indicating certain embodiments of the invention, are given by way of illustration only. Various changes and modifications within the spirit and scope of the disclosed invention will become readily apparent to those skilled in the art from reading the following description and from reading the other parts of the present disclosure.

EXAMPLES

Example 1 cDNA Library Construction

A. Total RNA Isolation

Total RNA was isolated from maize tissues with TRIzol Reagent (Life Technology Inc. Gaithersburg, Md.) using a modification of the guanidine isothiocyanate/acid-phenol procedure described by Chomczynski and Sacchi (*Anal. Biochem.* 162:156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase. Good results have been obtained using tissues such as night-harvested earshoot with husk at stage V-12 from corn line B73, corn night-harvested leaf tissue at stage V8-V10 from line B73, corn anther tissue at prophase I from line B73, 4 DAP coenocytic embryo sacs from corn line B73, 67 day old corn cob from corn line L, and corn BMS suspension cells treated with chemicals related to phosphatases.

B. Poly(A)+ RNA Isolation

The selection of poly(A)+ RNA from total RNA was performed using PolyATract system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

C. cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a NotI site. The reaction was catalyzed by Super-Script Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between NotI and SalI sites.

Example 2

Sequencing and cDNA Subtraction Procedures Used for Maize EST's

A. Sequencing Template Preparation

Individual colonies were picked and DNA was prepared either by PCR with M13 forward primers and M13 reverse primers, or by plasmid isolation. All the cDNA clones were sequenced using M13 reverse primers.

B. Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12-24 hours. Colonies were picked into 384- well plates by a robot colony picker, Q-bot (GENETIX Limited). These plates were incubated overnight at 37° C.

Once sufficient colonies were picked, they were pinned onto 22×22 cm² nylon membranes using Q-bot. Each membrane contained 9,216 colonies or 36,864 colonies. These membranes were placed onto individual agar plates with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40-50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in *Molecular Cloning: A Laboratory Manual, 2nd Edition*). The following probes were used in colony hybridization:
1. First strand cDNA from the same tissue from which the library was made to remove the most redundant clones.
2. 48-192 most redundant cDNA clones from the same library based on previous sequencing data.
3. 192 most redundant cDNA clones in the entire corn sequence database.
4. A Sal-A20 oligonucleotide: TCG ACC CAC GCG TCC GAA AAA AAA AAA AAA AAA AAA, removes clones containing a poly A tail but no cDNA. See SEQ ID NO: 26.
5. cDNA Clones Derived from rRNA.

The image of the autoradiography was scanned into computer and the signal intensity and cold colony addresses of each colony was analyzed. Re-arraying of cold-colonies from 384 well plates to 96 well plates was conducted using Q-bot.

Example 3

Identification and Isolation of ITPK Genes Using PCR

The maize ITPK-3, -5, and -6 genomic clones exemplified by SEQ ID NOS: 3, 7 and 9 respectively, were isolated by PCR using the commercially available Roche Expand High Fidelity PCR System. Template DNA was isolated using the CTAB method of Example 5C. The forward primer of SEQ ID NO: 15 was used with reverse primers SEQ ID NOS: 16,17, 22, or 27 to amplify the ITPK-5 gene from various maize lines. The buffer and polymerase concentrations were used as defined for the kit with the DNA concentrations and cycling conditions as follows:

DNA Concentrations:

500 ng template DNA and 0.3 µM primers in a 50 ul PCR reaction mixture containing 200 µM dNTPs in buffer and polymerase provided by the Roche kit.

Thermocycling conditions are as follows (#cycles):

| 1 cycle: | denature 2 min. at 94° C. |
|---|---|
| 10 cycles: | denature 15 sec. at 94° C. |
| | anneal 30 sec. at 55° C. |
| | elongate 60 sec. at 68° C. |

-continued

| 15 cycles: | denature 15 sec. at 94° C. |
|---|---|
| | anneal 30 sec at 55° C. |
| | elongate 60 sec. + 5 sec. each cycle at 68° C. |
| 1 cycle: | elongate 7 min. at 72° C. |

The products of the PCR reaction were analyzed on agarose gels using standard molecular biology techniques.

Similar to the *Arabidopsis* genomic clone (TIGR *Arabidopsis* database, At5g16760), it was found that the maize B73 ITPK-5 genomic sequence has no introns.

Example 4

Vector Construction

All vectors are constructed using standard molecular biology techniques used by those of skill in the art (Sambrook et al., supra).

A. Vectors for Plant Transformation

Vectors were constructed for plant transformation using either particle bombardment or *Agrobacterium* transformation protocols.

Plasmids were constructed by inserting ITPK-5 expression cassettes, including the following: oleosin promoter:ITPK-5:nos terminator, oleosin promoter:Sh1 intron:ITPK-5:nos terminator, oleosin promoter:ubiquitin intron:ITPK-5:nos terminator or globulins promoter:ITPK-5:globulin1 terminator, into a descendent plasmid of pSB11 which contains the BAR expression cassette. Both the ITPK-5 and the BAR expression cassettes were located between the right and left borders of the T-DNA.

For example, the *Zea mays* ITPK-5 coding region, including the 5' UTR and 3' UTR was isolated from a full length PCR clone as a 1.4 kb XhoII/SacI fragment. The fragment was inserted in-frame into a SacII/SalI-digested plasmid between the globulin1 promoter and terminator. The globulin1 promoter:ITPK-5:globulin1 terminator transcription unit was moved as a 2.94 kb HindIII/HpaI fragment into a second intermediate vector in order to flank the transcription unit with BstEII sites. These BstEII sites were used to excise the fragment and insert it into a binary vector containing the BAR selectable marker. The ITPK-5 cassette is linked to the selectable marker between the right and left borders of the T-DNA. This vector was used for insert preparation for particle gun transformation as well as for generating *Agrobacterium* transformation vectors as described below. In this case, insert DNA for particle gun transformation was generated by isolating the 6.6 kb PmeI fragment from the vector.

In other examples, ITPK-5 cassettes were linked with transcription units for the *Zea mays* inositol polyphosphate kinase (IPPK) or myo-inositol 1-phosphate synthase (MI1 PS-3) polynucleotides similarly constructed for expression in the maize embryo. IPPK polynucleotide sequences are disclosed in U.S. application Ser. No. 10/042,894 filed Jan. 9, 2002, MI1PS polynucleotide sequences are disclosed in WO 99/05298, the contents of which are herein incorporated by reference in their entirety. Alternatively, convenient restriction sites were used to fuse portions of the ITPK-5 coding sequence with portions of the coding sequence of IPPK or other ITPK polynucleotides to generate chimeric transcripts. Such stacked or linked expression cassettes were also inserted into derivatives of pSB11 with the BAR selectable marker as described above.

The plasmid pSB11 was obtained from Japan Tobacco Inc. (Tokyo, Japan). The construction of pSB11 from pSB21 and the construction of pSB21 from starting vectors is described by Komari et al. (1996, *Plant J.* 10:165-174). The T-DNA of the plasmid was integrated in to the superbinary plasmid pSB1 (Saito et al. EP 672 752 A1) by homologous recombination between the two plasmids. The plasmid pSB1 was also obtained from Japan Tobacco Inc. These plasmids were either used for particle bombardment transformation, or for *Agrobacterium*-mediated transformation after making a cointegrate in an appropriate *Agrobacterium* strain as described more fully below.

Competent cells of the *Agrobacterium* strain LBA4404 harboring pSB1 were created using the protocol as described by Lin (1995) in *Methods in Molecular Biology*, ed. Nickoloff, J. A. (Humana Press, Totowa, N.J.). The plasmid containing the expression cassettes was electroporated into competent cells of the *Agrobacterium* strain LBA4404 harboring pSB1 to create the cointegrate plasmid in *Agrobacterium*. Cells and DNA were prepared for electroporation by mixing 1 µl of plasmid DNA (~100 ng) with 20 µl of competent *Agrobacterium* cells in a 0.2 cm electrode gap cuvette (Bio-Rad Cat# 165-2086, Hercules, Calif.). Electroporation was performed in a Bio-Rad Micropulser (Cat# 165-2100, Hercules, Calif.) using the EC2 setting, which delivers 2.5 kV to the cells. Successful recombination was verified by restriction analysis of the plasmid after transformation of the cointegrate plasmid back into *E. coli* DH5α cells.

B. Vectors for In Vitro Protein Expression in *E. coli*

Vectors were constructed for protein expression of ITPK-2, ITPK-3 and ITPK-5 (SEQ ID NOS: 1, 3, and 7) in *E. coli* using standard protocols. Each ITPK sequence was fused with GST to produce GST-tagged proteins.

Cloning sites were introduced into the ITPK-2 sequence by PCR with the primers of SEQ ID NOS: 18 and 19. The primer of SEQ ID NO: 18 introduces a SmaI site to the 5' end of the ITPK-2 sequence, while the primer of SEQ ID NO: 19 introduces a NotI site to the 3' end of the sequence. Using these restriction sites, the ITPK-2 sequence was cloned into the pGEX-4T-2 vector (PHARMACIA BIOTECH) to generate the ITPK-2 GST-tagged expression vector PHP16334.

In the same way, the ITPK-3 GST-tagged expression construct PHP16335 was made using PCR primer SEQ ID NOS: 20 and 21 to introduce a 5' SmaI site and a 3' NotI site to the ITPK-3 sequence.

The ITPK-5 GST-tagged expression construct was made by first using the primer pair of SEQ ID NOS: 15 and 22 to generate the ITPK-5 insert. This insert was cloned into the pCR vector (INVITROGEN TA Cloning kit). The ITPK-5 pCR vector was digested with EcoRI and cloned into the pGEX-4T-1 vector (Pharmacia Biotech). Insert orientation was confirmed using a restriction enzyme digest.

These expression vectors were used to transform *E. Coli* strain DH5α using standard techniques. The expression of GST-tagged ITPK proteins and assay for substrate-specificity is further described in Example 7.

Example 5

Plant Transformation

A. Particle Bombardment Transformation and Regeneration of Maize Callus

Immature maize embryos from greenhouse or field grown High type II donor plants are bombarded with a plasmid comprising an ITPK polynucleotide of the invention operably linked to an appropriate promoter. If the polynucleotide does not include a selectable marker, another plasmid containing a selectable marker gene can be co-precipitated on the particles used for bombardment. For example, a plasmid containing the PAT gene (Wohlleben et al. (1988) *Gene* 70:25-37) which confers resistance to the herbicide Bialaphos can be used. Transformation is performed as follows.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These are cultured on 560L agar medium 4 days prior to bombardment in the dark. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

A plasmid vector comprising a polynucleotide of the invention operably linked to the selected promoter is constructed. This plasmid DNA, plus plasmid DNA containing a PAT selectable marker if needed, is precipitated onto 1.1 µm (average diameter) tungsten pellets using a $CaCl_2$ precipitation procedure as follows: 100 µl prepared tungsten particles (0.6 mg) in water, 20 µl (2 µg) DNA in TrisEDTA buffer (1 µg total), 100 µl 2.5 M $CaCl_2$, 40 µl, 0.1 M spermidine.

Each reagent is added sequentially to the tungsten particle suspension. The final mixture is sonicated briefly. After the precipitation period, the tubes are centrifuged briefly, liquid removed, washed with 500 ml 100% ethanol, and centrifuged again for 30 seconds. Again the liquid is removed, and 60 µl 100% ethanol is added to the final tungsten particle pellet. For particle gun bombardment, the tungsten/DNA particles are briefly sonicated and 5 µl spotted onto the center of each macrocarrier and allowed to dry about 2 minutes before bombardment.

The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Four to 12 hours post bombardment, the embryos are moved to 560P (a low osmoticum callus initiation medium similar to 560L but with lower silver nitrate), for 3-7 days, then transferred to 560R selection medium, an N6 based medium similar to 560P containing 3 mg/liter Bialaphos, and subcultured every 2 weeks. After approximately 10 weeks of selection, callus clones are sampled for PCR and activity of the polynucleotide of interest. Positive lines are transferred to 288J medium, an MS-based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to ClASSIC™ 600 pots (1.6 gallon) and grown to maturity. Plants are monitored for expression of the polynucleotide of interest.

B. *Agrobacterium*-mediated Transformation and Regeneration of Maize Callus

For *Agrobacterium*-mediated transformation of maize, an ITPK polynucleotide sequence of the present invention is used with the method of Zhao (U.S. Pat. No. 5,981,840, and PCT patent publication WO98/32326; the contents of which are hereby incorporated by reference).

Briefly, immature embryos are isolated from maize and the embryos contacted with a suspension of *Agrobacterium* containing a polynucleotide of the present invention, where the bacteria are capable of transferring the nucleotide sequence of interest to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

C. Transformation of Dicots with Transgene

An expression cassette, with an ITPK polynucleotide of the present invention operably linked to appropriate regulatory elements for expression, can be introduced into embryogenic suspension cultures of soybean by particle bombardment using essentially the methods described in Parrott, W. A., L. M. Hoffman, D. F. Hildebrand, E. G. Williams, and G. B. Collins, (1989) Recovery of primary transformants of soybean, *Plant Cell Rep.* 7:615-617. This method, with modifications, is described below.

Seed is removed from pods when the cotyledons are between 3 and 5 mm in length. The seeds are sterilized in a bleach solution (0.5%) for 15 minutes after which time the seeds are rinsed with sterile distilled water. The immature cotyledons are excised by first cutting away the portion of the seed that contains the embryo axis. The cotyledons are then removed from the seed coat by gently pushing the distal end of the seed with the blunt end of the scalpel blade. The cotyledons are then placed (flat side up) SB1 initiation medium (MS salts, B5 vitamins, 20 mg/L 2,4-D, 31.5 g/l sucrose, 8 g/L TC Agar, pH 5.8). The Petri plates are incubated in the light (16 hr day; 75-80 µE) at 26° C. After 4 weeks of incubation the cotyledons are transferred to fresh SB1 medium. After an additional two weeks, globular stage somatic embryos that exhibit proliferative areas are excised and transferred to FN Lite liquid medium (Samoylov, V. M., D. M. Tucker, and W. A. Parrott (1998) Soybean [*Glycine max* (L.) Merrill] embryogenic cultures: the role of sucrose and total nitrogen content on proliferation. In Vitro *Cell Dev. Biol.—Plant* 34:8-13). About 10 to 12 small clusters of somatic embryos are placed in 250 ml flasks containing 35 ml of SB172 medium. The soybean embryogenic suspension cultures are maintained in 35 mL liquid media on a rotary shaker, 150 rpm, at 26° C. with florescent lights (20 µE) on a 16:8 hour day/night schedule. Cultures are sub-cultured every two weeks by inoculating approximately 35 mg of tissue into 35 mL of liquid medium.

Soybean embryogenic suspension cultures are then transformed using particle gun bombardment (Klein et al. (1987) *Nature* (London) 327:70; U.S. Pat. No. 4,945,050). A BioRad BIOLISTIC™ PDS1000/HE instrument can be used for these transformations. A selectable marker gene, which is used to facilitate soybean transformation, is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is agitated for three minutes, spun in a microfuge for 10 seconds and the supernatant removed. The DNA-coated particles are washed once in 400 µL 70% ethanol and resuspended in 40 µL of anhydrous ethanol. The DNA/particle suspension is sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. Membrane rupture pressure is set at 1100 psi and the chamber is evacuated to a vacuum of 28 inches mercury. The tissue is placed approximately 8 cm away from the retaining screen, and is bombarded three times. Following bombardment, the tissue is divided in half and placed back into 35 ml of FN Lite medium.

Five to seven days after bombardment, the liquid medium is exchanged with fresh medium. Eleven days post bombardment the medium is exchanged with fresh medium containing 50 mg/mL hygromycin. This selective medium is refreshed weekly. Seven to eight weeks post bombardment, green, transformed tissue will be observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos, or tissue is regenerated into whole plants by maturation and germination of individual embryos.

D. DNA Isolation from Callus and Leaf Tissues

In order to screen putative transformation events for the presence of the transgene, genomic DNA is extracted from calli or leaves using a modification of the CTAB (cetyltriethylammonium bromide, Sigma H5882) method described by Stacey and Isaac (1994). Approximately 100-200 mg of frozen tissues is ground into powder in liquid nitrogen and homogenised in 1 ml of CTAB extraction buffer (2% CTAB, 0.02 M EDTA, 0.1 M Tris-Cl pH 8, 1.4 M NaCl, 25 mM DTT) for 30 min at 65° C. Homogenised samples are allowed to cool at room temperature for 15 min before a single protein extraction with approximately 1 ml 24:1 v/v chloroform: octanol is done. Samples are centrifuged for 7 min at 13,000 rpm and the upper layer of supernatant collected using widemouthed pipette tips. DNA is precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five µl RNAse A is added to the samples and incubated at 37° C. for 1 h.

For quantification of genomic DNA, gel electrophoresis is performed using a 0.8% agarose gel in 1×TBE buffer. One microlitre of the samples are fractionated alongside 200, 400, 600 and 800 ng µl$^{-1}$ λ uncut DNA markers.

Example 6

Identification of High Phosphorus/Low Phytate Transgenic Corn Lines

The resulting transformants are screened for inorganic phosphorus and/or phytate levels using the colorimetric assays as described below. The extraction procedure used is compatible with both assays. The colorimetric assays can be performed sequentially or simultaneously. Putative events are usually initially screened for increased levels of inorganic phosphorous compared to wild type control and then further characterized by the phytate assay.

A. Sample Preparation

Individual kernels are crushed to a fine powder using a ball mill grinding device. Grinding of certain samples, for example high oil corn lines, can be facilitated by chilling the sample in the grinding apparatus at −80° C. for 2 hours prior to grinding. Transfer 25-35 mg of each ground sample to new 1.5 ml microfuge tube. Extract each sample with 1 ml of 0.4N hydrochloric acid (HCl) for 3.5 hours at room temperature with shaking to keep the meal suspended. Transfer 1 ml of this suspension to a 1.1 ml Megatiter tube (Cat# 2610, Continental Labs) and place into the 96-well Megatiter plate (Cat# 2405, Continental Labs). Clarify the extract by low-speed centrifugation, for example 4000 rpm for 15 minutes in a Jouan centrifuge. The clarified supernatant is used for the assays described in sections 6B and 6C below.

B. Quantitative Inorganic Phosphate Assay

This assay is performed in duplicate for each sample according to the method of Chen, et al. (1956 *Anal. Chem.* 28:1756-1758) with some modifications. For each sample, mix a 200 ul aliquot of clarified extract with 100 µl 30% trichloroacetic acid (TCA). Clarify by low speed centrifugation at 3900×g for 10 min. Transfer 50 µl clarified supernatant to a new 96-well microtiter plate. Add 100 µl of the color reagent (7 parts 0.42% ammonium molybdate in 1 N H2SO4: 1 part 10% ascorbic acid) and incubate at 37° C. for 30 minutes. A phosphate standard curve is generated using NaH$_2$PO$_4$ in the range of 0-160 nmol diluted from a 10 mM stock solution in 2 parts 0.4N HCl: 1 part 30% TCA. Measure the absorbance at 800 nm.

C. Quantitative Phytate Assay

This assay is modified from Haug and Lantzsch (1983) *J. Sci. Food Agric.* 34:1423-1426. This assay is performed in duplicate for each sample. Phytate standard (Cat# P-7660, Sigma Chemical Co., St. Louis, Mo.) stock solution is made by dissolving 150 mg phytate in 100 ml distilled water (DDW). Standards in the range of 0-35 µg/ml are made by dilution with 0.2N HCl. Samples are prepared in 96-well microtiter plates by mixing 35 µl of clarified supernatant (from 6A) with 35 µl of DDW, add 140 µl ferric solution (0.2 g ammonium iron (III) sulphate dodecahydrate (Merck Art 3776)/liter in 0.2N HCl). Plates are sealed and incubated for 30 minutes at 99° C., then cooled to 4° C. Plates are kept in an ice-water bath for 15 minutes then transferred to room temperature for 20 minutes. Centrifuge the plates at low speed to pellet precipitate, for example spin 30 minutes at 4000 rpm in a Jouan centrifuge. After centrifugation transfer 80 µl clarified supernatant to a new 96-well plate and mix with 120 ul 1% 2,2'-bipyridine-1% thioglycollic acid solution (10 g 2,2'-bipyridine (Merck Art. 3098), 10 ml thioglycolic acid (Merck Art. 700) in DDW to 1 liter). The absorbance at 519 nm is read using a VERSAmax microplate reader (Molecular Devices, Sunnyvale, Calif.).

Each plant identified as a potential high available phosphorus transgenic is tested again to confirm the original elevated phosphorus reading. Confirmed high available phosphorous lines are selected on the basis of uniformity for the trait. Transformants which are positive with the colorimetric assays can then be subjected to more rigorous analyses to include Southern, Northern and Western blotting and/or quantitation and identification of phytic acid and inositol phosphate intermediates by HPLC.

Example 7

Determining the Substrate Specificity of the ITPK Clones

A. Expression of ITPK and Purification

A single colony of *E. coli* strain DH5α containing a GST-tagged ITPK expression vector described in Example 4 is cultured overnight at 37° C. in LB medium containing ampicillin (Amp). The overnight culture is diluted 1:10 with fresh LB+Amp and incubated at 37° C. with vigorous agitation until the A600 reading of the culture is in the range of 0.6-2 O.D. units. GST fusion protein expression is induced by the addition of IPTG to the culture to a final concentration of 50 µM. The cultures are incubated at 37° C. with agitation for an additional 3 hrs.

Cells are harvested by centrifugation at 7,700×g for 10 minutes at 4° C. Cell pellets are resuspended in ice-cold bacterial lysis buffer (50 mM Tris-HCl, pH 7,4, 100 mM NaCl, 100 µM phenylmethylsulfonyl fluoride). The cells are lysed on ice by sonication, then Triton X-100 is added to a final concentration of 1%. After incubation on ice for 1 hour, the lysate is clarified by centrifugation at 12,000×g for 10 minutes at 4° C. The GST-ITPK proteins are affinity purified by batch absorption to Glutathione Sepharose 4B bead resin (Bulk GST Purification kit, Pharmacia Biotech) at a ratio of 1 ml bed volume of the 50% Glutathione Sepharose 4B slurry per 100 ml clarified lysate. The mixture is incubated 45 minutes at 4° C. with gentle shaking. Following the conditions detailed in the manufacturer's instructions, the beads are washed four times in lysis buffer, then two times in phosphate buffered saline. GST-tagged ITPK protein is eluted with 10 mM reduced glutathione in 50 mM Tris-HCl (pH8.0), 100 mM NaCl. For every 500 ml of cell culture, 200 µl buffer is used to elute the protein. After elution, glycerol is added to a final concentration of 50% and purified GST-ITPK proteins are stored in 50% glycerol at −20° C.

B. Assay for ITPK Activity and Substrate Specificity

Inositol phosphate kinase activities are assayed according to Wilson and Majerus (1996 *J. Biol. Chem.* 271:11904-11910) with some modifications. This assay cannot identify the stereospecific structure of the inositol phosphate product, but it does demonstrate the inositol phosphate kinase activity of the protein of interest.

Purified GST-ITPK fusion proteins are used in an inositol 1,3,4-trisphosphate 5/6-kinase activity assay. The activity assay is performed in a volume of 25 µl. The assay mixture contains 20 mM HEPES, pH 7.2, 6 mM $MgCl_2$, 10 mM LiCl, 1 mM DTT, 40 µM Ins(1,3,4)$P_3$, 40 µM ATP, 0.5 µl γ-$^{32}$P-ATP (3000 Ci/mmol) and 5 µl enzyme per reaction. The reaction mixture is incubated at 30° C., or room temperature, for 30 minutes. The reaction is stopped by the addition of 2.8 µl stopping solution (3M HCl, 2M $KH_2PO_4$) to the 25 µl reaction. One microliter samples of each reaction, along with Ins(1,3,4,5)$P_4$ and Ins(1,3,4,6)$P_4$ standards, are separated on a polyethyleneimine (PEI)-cellulose thin layer chromatography plate (Merck) with 0.5M HCl according to Spencer et al. (*In Methods in Inositide Research*, (1990) pp. 39-43, Ed. R. F. Irvine, Raven Press, NY). After separation, the TLC plate is air-dried at 70° C., wrapped in plastic wrap and exposed to X-ray film to detect the $^{32}$P-labelled reaction products. The reaction products are quantified by cutting the spot out of the TLC plate and measuring the radioactivity in a liquid scintillation counter. The identity of the reaction product is confirmed by comparing the distance migrated to the migration of the Ins$P_4$ standard controls run on each TLC plate. In addition to the Ins(1,3,4)$P_3$, other inositol phosphate substrates are also tested to determine the substrate specificity of the ITPK enzymes. The other substrates tested under the same conditions above included: Ins(1)P, Ins(2)P, Ins(4)P, Ins(1,4)$P_2$, Ins(4,5)$P_2$, Ins(3,5,6)$P_3$, Ins(1,4,5)$P_3$, Ins(2,4,5)$P_3$, Ins(3,4,5,6)$P_4$, Ins(1,3,4,6)$P_4$, Ins(1,3,5,6)$P_4$, Ins(1,2,5,6)$P_4$, Ins(1,3,4,5)$P_4$, and Ins(1,3,4,5,6)$P_5$.

Assay results indicated that each of ITPK-2, ITPK-3 and ITPK-5 are capable of phosphorylating the Ins(1,3,4)$P_3$ substrate to produce $^{32}$P-labelled products that comigrate with Ins(1,3,4,5)$P_4$ and Ins(1,3,4,6)$P_4$ on PEI-cellulose TLC plates, confirming the expected activity of the enzymes. Further, the ITPKs tested could also use Ins(3,5,6)$P_3$, Ins(3,4,5,6)$P_4$ and Ins(1,2,5,6)$P_4$ as a substrate in the in vitro assay. When Ins(3,4,5,6)$P_4$ was used as a substrate, the product comigrated with Ins(1,3,4,5,6)$P_5$, indicating the enzyme can also act as a Ins(3,4,5,6)$P_4$ 1-kinase. The Ins(3,4,5,6) 1-kinase activity was also reported for a human ITPK enzyme (Yang, X. and Shears, S. B. (2000) *Biochem J*. 351:551-555; Ho et al. (2002) *Curr Biol* 12:477-482). Ins(1,4,5)P3 3-kinase activity has been reported for Ins(1,3,4)P3 5/6-kinase in *Entamoeba histolytica* (Field et al. (2000) *Mol Biochem Parasitol* 108: 119-123). When the substrate Ins(1,3,4,5)$P_4$ was used with ITPK-5, weak kinase activity was detected and 2 products, an Ins$P_4$ and an Ins$P_5$, were produced. No kinase activity was detected when any of Ins(1)P, Ins(2)P, Ins(4)P, Ins(1,4)$P_2$, Ins(4,5)$P_2$, Ins(1,4,5)$P_3$, Ins(2,4,5)$P_3$, Ins(1,3,4,6)$P_4$, Ins(1,3,5,6)$P_4$, or Ins(1,3,4,5,6)$P_5$ were used as substrates in the reaction mixture.

Example 8

ITPK Corn Knockout Mutants

Mu-tagged corn populations (TUSC) (Bensen, R J, et al. (1995) *Plant Cell* 7:75-84) are screened for knockouts of the ITPK-5 gene (SEQ ID NO: 7), using the primers of SEQ ID NO: 23 or 24 paired with a Mu-primer SEQ ID NO: 25 in PCR reactions. From a collection of about 40,000 Mu-insertion lines, four independent lines were identified as having a Mu-insertion in the ITPK-5 gene, these lines are designated ITPK5-Mum1, ITPK5-Mum2, ITPK5-Mum3, and ITPK5-Mum4, or ITPK5-Mum collectively. Kernels from three of these lines were screened for phytate and inorganic phosphate levels versus phytate mutants Lpa1 and Lpa2, as well as wild type controls, using the assays described in Example 6.

Analysis of individual ITPK5-Mum F2 seeds for phytic acid and organic phosphate ($P_i$) showed that about 25% of F2 seeds had a reduced level of phytic acid and an increased level of $P_i$, while 75% of F2 seeds showed phytic acid and $P_i$ at wildtype levels. Similar phenotypes in four independent lines and this segregation ratio support the assumption that the low phytic acid phenotype is caused by Mu-insertion in the maize ITPK-5 gene.

The Mu-insertion was mapped for ITPK5-Mum lines by sequencing the Mu-ITPK-5 junction region. In ITPK5-Mum1, Mu is inserted at nucleotide position 237, which is amino acid position 61. The Mu insertion in ITPK5-Mum2 occurs at nucleotide position 245, which is amino acid position 64. In ITPK5-Mum3, the Mu insertion occurs at nucleotide position 366, which corresponds to amino acid 104. The Mu insertion in ITPK5-Mum4 is at nucleotide position 872, which is amino acid 273. In all lines, mapping demonstrated that Mu insertion disrupted the ITPK-5 open reading frame.

Genotyping individual F2 seeds confirmed that Mu was inserted in the ITPK-5 gene. Individual F2 seeds were ground to a fine powder. An aliquot of each meal was used to determine phytic acid and $P_i$, and the remaining meal used for DNA extraction and PCR analysis. PCR was done using the primer pair of SEQ ID NO: 15 and SEQ ID NO: 27, which flank the Mu insertion site. A PCR product of 1.3 KB is expected to be amplified from the intact ITPK-5 gene, but not from the ITPK5-Mum allele. Seeds with an ITPK-5/ITPK-5 or ITPK-5/ITPK5-Mum genotype will yield the 1.3 kb PCR fragment, but ITPK5-Mum/ITPK5-Mum seeds will not. It was found that the low phytic acid kernels did not contain an intact copy of the ITPK-5 gene, while the 1.3 kb DNA fragment was only amplified from kernels with normal phytic acid and $P_i$ levels. F3 and subsequent generations also showed the low phytic acid and high $P_i$ phenotype in all four ITPK5-Mum lines.

HPLC analyses for myo-inositol (Example 9) and inositol phosphates (Example 10) showed that in addition to the changes in kernel phytic acid and $P_i$, ITPK5-Mum lines also accumulate myo-inositol, Ins$P_3$, Ins$P_4$, and Ins$P_5$ in the embryo. No obvious differences were found in the endosperm.

Results indicate that relative to the wild type control, phytate was reduced by about 30%. Further, it was observed that inorganic phosphorous was increased to about 0.6 mg/g in the ITPK-5 TUSC line vs. 0.16 mg/g for the wild type control. Myo-inositol levels were increased above 170 µg/g in ITPK5-Mum vs. about 75-90 µg/g in the normal whole kernel control. In embryos only, myo-inositol levels were increased to about 438 µg/g in ITPK5-Mum vs. 254 µg/g in the wildtype control.

ITPK5-Mum lines have a phenotype very similar to Ipa2 mutants (Raboy et al. (2000) *Plant Physiol*. 124:355-368). Lpa2 is a recessive, low phytic acid mutant created by chemical mutagenesis, this mutant also accumulates Ins$P_3$, Ins$P_4$, Ins$P_5$ and $P_i$ in the seeds. We also found that the embryo of Ipa2 mutant seeds accumulate myo-inositol, similar to the ITPK5-Mum lines, to about 614 µg/g. No gene or genes have been identified as being responsible for the Ipa2 phenotype. Crosses between ITPK5-Mum3 and Ipa2-1 and Ipa2-2 were performed to determine if the genes are allelic.

Before crossing, all lines were backcrossed with inbreds to reduce background effects. ITPK5-Mum3 was crossed with maize inbred line PHP38 to reduce Mu copy number. The ITPK5-Mum3 allele was tracked by monitoring the low phytate phenotype of corresponding selfed ears. After three backcrosses, the ITPK5-Mum3 line was selfed to produce ITPK5-Mum3 homozygotes. Lpa2 mutant lines were provided by Victor Raboy. The Ipa2-1 mutant allele line (Raboy et al. (2000) *Plant Physiol*. 124:355-368) was backcrossed twice with maize inbred PHJ90, then selfed to homozygosity. A second, separately isolated Ipa2 mutant allele line, Ipa2-2 (Raboy, personal communication), was backcrossed four times to inbred line PHN46, then selfed to homozygosity.

When homozygous ITPK5-Mum3 plants were crossed with the recessive Ipa2-1 and Ipa2-2 mutant lines, all the F1 seeds displayed the low phytic acid and high $P_i$ phenotype. When heterozygous ITPK5-Mum3 plants were crossed with Ipa2-2, the F1 seeds showed 1:1 mutant:wildtype phenotype segregation. This demonstrates that the Ipa2 mutant is a mutation in the ITPK-5 gene.

The ITPK-5 gene was amplified from the Ipa2-2 mutant using the primer pair of SEQ ID NO: 15 and SEQ ID NO: 27. Sequencing of the amplified DNA showed a point mutation of C to T at nucleotide position 158 (SEQ ID NO: 28). This mutation introduces a stop codon (TAG) at amino acid 35 instead of the glutamine (Gln) found in normal ITPK-5. Thus, Ipa2-2 appears to produce a severely truncated 34 amino acid polypeptide (SEQ ID NO: 29) which lacks inositol phosphate kinase activity based on the phenotype of the seeds.

PCR amplification of the ITPK-5 gene from the Ipa2-1 allele lines with the same primer pair did not produce any product. Southern analysis revealed differing band patterns between Ipa2-1 mutant vs. non-mutant near-isogenic lines using a 0.7 kb probe which covered nucleotides 367-1088. This region contains a BamHI restriction site and, as expected, two bands are detected in the non-mutant lines (~3.7 kb and ~1.4 kb). While the Ipa2-1 mutant line also showed two bands, the fragment were significantly larger (both >~8 kb). Restriction enzymes EcoRI, EcoRV, HindIII, and XbaI are absent from the probe region and, as expected, a single band was detected in the non-mutant line. However, XbaI digestion of Ipa2-1 mutant line reveals two fragments. HindIII digestion also produced two fragments (~0.7 kb and ~1.6 kb) not seen in the non-mutant ITPK-5 gene. These results indicate a rearrangement of the genomic sequence in the ITPK-5 locus of the Ipa2-1 mutant, likely producing the loss of an intact ITPK-5 gene in the mutant. RT-PCR was done on Ipa2-1 immature seeds, but no transcript could be detected.

Example 9

Myo-Inositol Assay

Putative events can also be screened to determine the effect the transgene may have on myo-inositol levels in the kernel using a gas chromatography/mass spectrometry method. Either whole, mature, dry kernels or excised embryos are assayed. Embryos are dissected from mature whole kernels after soaking dry seeds in double distilled water (DDW) four hours at 4° C. The isolated embryos are lyophilized, then ground for extraction as described below.

Whole, mature, dry kernels or embryos are ground to a fine meal in a ball mill apparatus. Each sample is analyzed in triplicate. For extraction, three aliquots of each sample is extracted with 50% v/v ethyl alcohol (1:1 100% ethyl alcohol: DDW) at a ratio of 0.1 g meal/1 ml 50% ethyl alcohol at room temperature for one hour with vigorous shaking. The extract supernatant is decanted and filtered through a 0.45 µm syringe filter. The meal residue is re-extracted with fresh 50% ethanol following the same procedure, combining the two filtrates. Each sample is vortexed, and a 1 ml aliquot taken and evaporated to dryness in a SpeedVac at medium heat.

A myo-inositol standard stock of 10 mg/ml is made in double distilled water (DDW) which is used to make a 1 mg/ml standard solution working stock. Aliquots of 50 µl, 100 µl, 200 µl and 300 µl are transferred to new tubes and evaporated to dryness in a SpeedVac as described above. This calibration set covers a concentration range of 5 µg/ml to 30 µg/ml of each component.

Thoroughly dried standards and samples are resuspended in 50 µl pyridine. To this, 50 µl of 100:1 trimethylsilylimadazole-trimethylchlorosilane (TMSI-TMCS) is added to each sample. Samples are compromised if a precipitate forms. Tubes are sealed, vortexed and incubated 15 min. at 60° C. After incubation, 1 ml of 2,2,4-trimethylpentane and 0.5 ml DDW are added. Vortex samples and centrifuge at low speed (2000 rpm) 1000×g for 5 minutes. The top, organic layer is transferred to a 2 ml autosampler vial and crimp sealed. At this point, the samples can be stored at 4° C. until analyzed.

Samples are analyzed on a Hewlett-Packard 5890/7673/5972 Gas Chromatography/Mass Spectrometry (GC/MS) apparatus using a Hewlett-Packard 30 m×0.25 mm i.d.×0.25 µm film thickness 5MS column under the following conditions:

| | |
|---|---|
| Inlet temperature: | 250° C. |
| Injection Volume: | 1 ml |
| Split Ratio: | Splitless |
| Oven Temperature: | 70° C. initial, hold for 2 min. |
| | Ramp at 25° C./min. to 170° C., hold for 0 min. |
| | Ramp at 5° C./min. to 215° C., hold for 0 min. |
| | Ramp at 25° C./min to 250° C., hold for 5 min. |
| | 23.4 min. total run time |
| Detector Temperature: | 250° C. |
| Carrier Gas: | Helium, 36.6 cm/sec at 70° (1 ml/min.) |

Full scan (m/z 50-650), acquired at −70 eV after 5 minute solvent delay. Results are reported as µg/ml for the final sample analyzed by the GC/MS, this concentration is multiplied by a factor of 20 before using to calculate µg/g dry weight tissue. The moisture content of the mature kernels is determined from a separate aliquot of each experimental sample so that the results can be adjusted to a dry weight basis.

Myo-inositol levels are quantified as follows:

$$\frac{\mu g\ myo\text{-inositol}}{g\ \text{dry wt. tissue}} = \frac{\mu g(\times 20)}{\text{ml sample}} \times \frac{1\ \text{ml sample}}{1\ \text{ml extract}} \times \frac{10\ \text{ml extract}}{0.5\ \text{g tissue}}$$

Regression coefficients of four-point calibration curves were typically 0.999-1.000.

Example 10

HPLC of Phytate and Inositol Phosphate Intermediates

Phytate and inositol phosphate intermediates associated with phytic acid in wheat, corn, and soybean seeds can be identified and quantitated using gradient anion-exchange chromatography HPLC with conductivity detection. While phytate and intermediate inositol phosphates can be identified using this method, the method practiced currently has been optimized for phytate, it is not optimized for quantitation of intermediate inositol phosphates. For other HPLC separations of inositol phosphates see also Anonymous, (1990) "Analysis of inositol phosphates" *Dionex Corp. Application Note AN* 65; Xu, P., Price, J., and Aggett, P. (1992) *Progress in Food and Nutrition Science* 16:245262; Rounds, M. A. and Nielsen, S. S. (1993) *J. Chromatogr* 653:148-152; and Trugo, L. and von Baer, D. (1998) *Association for animal production*, publication 93:1128. Inositol phosphates can also be identified by thin-layer chromatographic methods, see for example Spencer, C. E. L et al. (1990) Ch. 4 in *Methods in Inositide Research*, Ed. R. F. Irving, Raven Press, Ltd., NY pp. 3943; and Hatzack, F. and Rasmussen, S. K. (1999) *J. Chromatogr B* 736:221-229.

For anion-exchange HPLC, a phytic acid standard range of 0.25, 0.5, 1.0, 2.0 and 3.0 mg/ml is prepared in 0.4M hydrochloric acid (HCl) from a 20 mg/ml working stock in 0.4M HCl. Seed samples are prepared by grinding seeds to a fine meal in a ball mill grinding apparatus. Replicate aliquots are weighed and extracted in 0.4M HCl in a ratio of 0.1 g meal/1 ml 0.4M HCl. Usually 5 ml 0.4M HCl is used to extract 0.5 g corn or wheat meal while 15 ml 0.4M HCl is used to extract 1.5 g soy meal. After the addition of the extraction buffer, the samples are extracted with moderate-vigorous shaking for 2 hrs. at room temperature, then transferred to 4° C. overnight without shaking. The supernatants from corn and wheat are clarified by low-speed centrifugation at 1000×g for 10 minutes. Due to the high fat content, the low-speed supernatant from soy sample extracts is further clarified by ultracentrifugation at 55,000 rpm at 4° C. for 1 hour. After ultracentrifugation, the clear, middle layer is removed with a needle or extended tip disposable transfer pipette. Clarified samples are filtered through a 0.45 μm syringe filter and stored at 4° C. until analysis. Just before analysis, an aliquot of each sample is filtered with a Millipore Durapore ULTRAFREE-MC 0.22 μm centrifugal filter unit, or equivalent.

Using a Dionex DX500 HPLC with a Dionex model AS3500 autosampler, 25 microliter samples are subjected to anion-exchange HPLC separation by a linear gradient of 0.06-0.118M sodium hydroxide (NaOH) in 1% isopropyl alcohol on a Dionex 4×250 mm OmniPac PAX-100 column at a flow rate of 1 ml/min. Dionex 4×50 mm OmniPac PAX-100 guard and ATC-1 anion trap columns were used. The total run time is 30 min. with data collection from 0 to 20 minutes. A Dionex conductivity detector module II was used with a Dionex ASRS-Ultra II anion self-regenerating suppressor in the external water mode. Signal collection is set at 0.5 Hz, detector units in μS, current at 300 mA, with the Detection Stablilizer regulated at 30° C. and temperature compensation at 1.7.

Soybean samples appear to cause column performance deterioration, therefore it is helpful to interject short column cleaning run between samples. The cleaning run comprises a series of injections for 1 M HCl, 1 M NaOH, and 90% acetonitrile.

Chromatographic traces show that $InsP_3$, $InsP_4$, and $InsP_5$ are partially, but clearly resolved from each other and $InsP_6$.

Example 11

ITPK5 mRNA Expression

Northern blotting analysis is conducted to reveal any developmental and/or tissue specific mRNA expression patterns for ITPK5. The analysis is conducted using standard molecular biology protocols such as those found in *Current Protocols in Molecular Biology* (Ausubel et al., Eds., Greene Publishing and Wiley-Interscience, New York, 1995); *Plant Molecular Biology: A Laboratory Manual* (Clark, Ed., Springer-Verlag, Berlin, 1997); and *Molecular Cloning: A Laboratory Manual*, $2^{nd}$ Ed. (Sambrook et al., Cold Spring Harbor Laboratory, Vols 1-3, 1989), herein incorporated by reference.

Northern blotting analysis was conducted using total RNA at different developmental stages from various tissues from corn line B73. The tissues tested include 7 and 11 DAP whole kernel, 15, 22, 29, and 35 DAP endosperm, 15, 22, 29, and 35 DAP embryo, stalk, stem, leaf, silk, 0 DAP cob, brace root, and husk tissues. RNA was prepared using the Purescript RNA isolation kit (Gentra, Minneapolis, Minn.). Ten micrograms of RNA were resolved on 1% agarose/formaldehyde/MOPS gels and transferred to nylon membranes using standard conditions. Preparation of the ITPK5 probe, hybridization, and washing were carried out according to the manufacturer's instructions.

The maize ITPK5 gene transcript expression peaks in the embryo at 15 days after pollination (DAP). Expression could be detected in embryos at earlier stages, but at very low levels. Expression peaks at 15 DAP, then declines at later stages. No expression was detected from endosperm or vegetative tissues.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated nucleic acid comprising a member selected from the group consisting of:
   (a) a polynucleotide having the sequence set forth SEQ ID NO: 7;
   (b) a polynucleotide which encodes the polypeptide of SEQ ID NO: 8; and
   (c) a polynucleotide which is fully complementary to a polynucleotide of (a) through (b).

2. The isolated nucleic acid of claim 1, wherein the polynucleotide is from a plant.

3. A vector comprising at least one nucleic acid of claim 1.

4. An expression cassette comprising at least one nucleic acid of claim 1 operably linked to a promoter.

5. The expression cassette of claim 4 further comprising any combination of additional polynucleotide sequences of interest.

* * * * *